United States Patent
Phan et al.

(10) Patent No.: US 7,462,162 B2
(45) Date of Patent: Dec. 9, 2008

(54) ANTIPROLIFERATIVE DEVICES FOR MAINTAINING PATENCY OF SURGICALLY CREATED CHANNELS IN A BODY ORGAN

(75) Inventors: Loc Phan, San Jose, CA (US); Ed Roschak, Mission Viejo, CA (US)

(73) Assignee: Broncus Technologies, Inc., Mountain View, CA (US)

( * ) Notice: Subject to any disclaimer, the term of this patent is extended or adjusted under 35 U.S.C. 154(b) by 235 days.

(21) Appl. No.: 10/895,010

(22) Filed: Jul. 19, 2004

(65) Prior Publication Data

US 2005/0043752 A1 Feb. 24, 2005

Related U.S. Application Data

(63) Continuation-in-part of application No. 10/458,085, filed on Jun. 9, 2003, and a continuation-in-part of application No. 10/235,240, filed on Sep. 4, 2002.

(60) Provisional application No. 60/317,338, filed on Sep. 4, 2001.

(51) Int. Cl.
*A61M 5/00* (2006.01)
*A61B 17/08* (2006.01)
*A61F 2/04* (2006.01)

(52) U.S. Cl. .................. 604/8; 606/155; 623/23.65

(58) Field of Classification Search ............... 604/8–10, 604/4.01–6.16; 623/1.1–2.42, 11.11, 23.64–23.71; 606/153, 109, 185, 195, 155
See application file for complete search history.

(56) References Cited

U.S. PATENT DOCUMENTS

| | | | |
|---|---|---|---|
| 2,127,903 A | 8/1938 | Bowen | |
| 3,174,851 A | 3/1965 | Buehler et al. | |
| 3,351,463 A | 11/1967 | Rozner et al. | |
| 3,433,226 A | 3/1969 | Boyd | |
| 3,556,079 A | 1/1971 | Omizo | |
| 3,565,062 A | 2/1971 | Kuris | |
| 3,617,060 A | 11/1971 | Leggi | |
| 3,707,151 A | 12/1972 | Jackson | |
| 3,753,700 A | 8/1973 | Harrison et al. | |
| 3,779,234 A | 12/1973 | Eggleton et al. | |
| 3,823,717 A | 7/1974 | Pohlman et al. | |
| 3,874,388 A | 4/1975 | King et al. | |
| 3,889,688 A | 6/1975 | Eamkaow | |
| 3,942,530 A | 3/1976 | Northeved | |
| 4,249,539 A | 2/1981 | Vilkomerson et al. | |
| 4,249,541 A | 2/1981 | Pratt | |

(Continued)

OTHER PUBLICATIONS

Grippi, M. et al., "Emphysema," *Lippincotts' Pathophysiology Series*: Pulmonary.
Paterra, TM, (Version 1.5) Machine Translation of JP 2000-107178, 1-31.
White, R., et al., "Peripheral Endovascular Interventions," Mosby & Co, 166-169, 1996.

* cited by examiner

*Primary Examiner*—Leslie R Deak
*Assistant Examiner*—Phil Wiest
(74) *Attorney, Agent, or Firm*—Levine Bagade Han LLP

(57) ABSTRACT

This is directed to methods and devices suited for maintaining an opening in a wall of a body organ for an extended period. More particularly devices and methods are directed maintaining patency of channels that alter gaseous flow within a lung to improve the expiration cycle of, for instance, an individual having chronic obstructive pulmonary disease.

32 Claims, 12 Drawing Sheets

U.S. PATENT DOCUMENTS

| | | | |
|---|---|---|---|
| 4,319,580 A | 3/1982 | Colley et al. |
| 4,324,235 A | 4/1982 | Beran |
| 4,355,426 A | 10/1982 | MacGregor |
| 4,407,294 A | 10/1983 | Vilkomerson |
| 4,431,006 A | 2/1984 | Trimmer et al. |
| 4,503,569 A | 3/1985 | Dotter |
| 4,534,761 A | 8/1985 | Raible |
| 4,538,606 A | 9/1985 | Whited |
| 4,538,618 A | 9/1985 | Rosenberg et al. |
| 4,582,067 A | 4/1986 | Silverstein et al. |
| 4,583,969 A | 4/1986 | Mortensen |
| 4,658,817 A | 4/1987 | Hardy |
| 4,674,498 A | 6/1987 | Stasz |
| 4,676,782 A | 6/1987 | Yamamoto et al. |
| 4,682,596 A | 7/1987 | Bales et al. |
| 4,687,482 A | 8/1987 | Hanson |
| 4,750,902 A | 6/1988 | Wuchinich et al. |
| 4,753,236 A | 6/1988 | Healey |
| 4,757,821 A | 7/1988 | Snyder |
| 4,757,822 A | 7/1988 | Di Giuliomaria et al. |
| 4,767,627 A | 8/1988 | Caldwell et al. |
| 4,769,031 A | 9/1988 | McGough et al. |
| 4,770,185 A | 9/1988 | Silverstein et al. |
| 4,771,788 A | 9/1988 | Millar |
| 4,773,413 A | 9/1988 | Hussein et al. |
| 4,785,402 A | 11/1988 | Matsuo et al. |
| 4,795,465 A | 1/1989 | Marten |
| 4,802,476 A | 2/1989 | Noerenberg et al. |
| 4,807,634 A | 2/1989 | Enjoji et al. |
| 4,808,153 A | 2/1989 | Parisi |
| 4,834,102 A | 5/1989 | Schwarzchild et al. |
| 4,869,268 A | 9/1989 | Yoon |
| 4,870,953 A | 10/1989 | Don Micheal et al. |
| 4,887,606 A | 12/1989 | Yock et al. |
| 4,892,098 A | 1/1990 | Sauer |
| 4,892,099 A | 1/1990 | Ohkawa et al. |
| 4,899,757 A | 2/1990 | Pope, Jr. et al. |
| 4,917,097 A | 4/1990 | Proudian et al. |
| 4,920,954 A | 5/1990 | Alliger et al. |
| 4,924,863 A | 5/1990 | Sterzer |
| 4,936,281 A | 6/1990 | Stasz |
| 4,955,377 A | 9/1990 | Lennox et al. |
| 4,957,508 A | 9/1990 | Kaneko et al. |
| 4,967,753 A | 11/1990 | Haase et al. |
| 4,973,301 A | 11/1990 | Nissenkorn |
| 4,977,898 A | 12/1990 | Schwarzschild et al. |
| 5,002,058 A | 3/1991 | Martinelli |
| 5,030,201 A | 7/1991 | Palestrant |
| 5,054,483 A | 10/1991 | Marten et al. |
| 5,061,275 A | 10/1991 | Wallsten et al. |
| 5,064,435 A | 11/1991 | Porter |
| 5,069,664 A | 12/1991 | Suess et al. |
| 5,081,993 A | 1/1992 | Kitney et al. |
| 5,100,423 A | 3/1992 | Fearnot |
| 5,105,816 A | 4/1992 | Shimura et al. |
| 5,105,817 A | 4/1992 | Uchibori et al. |
| 5,123,917 A | 6/1992 | Lee |
| 5,125,926 A | 6/1992 | Linhares et al. |
| 5,127,917 A | 7/1992 | Niederhauser et al. |
| 5,131,394 A | 7/1992 | Gehlbach |
| 5,148,809 A | 9/1992 | Biegeleisen-Knight et al. |
| 5,178,635 A | 1/1993 | Gwon et al. |
| 5,190,528 A | 3/1993 | Fonger et al. |
| 5,201,316 A | 4/1993 | Pomeranz et al. |
| 5,209,721 A | 5/1993 | Wilk |
| 5,220,924 A | 6/1993 | Frazier |
| 5,226,421 A | 7/1993 | Frisbie et al. |
| 5,254,112 A | 10/1993 | Sinofsky et al. |
| 5,257,990 A | 11/1993 | Nash |
| 5,259,385 A | 11/1993 | Miller et al. |
| 5,261,409 A | 11/1993 | Dardel |
| 5,263,992 A * | 11/1993 | Guire ..................... 623/66.1 |
| 5,269,326 A | 12/1993 | Verrier |
| 5,273,529 A | 12/1993 | Idowu |
| 5,275,166 A | 1/1994 | Vaitekunas et al. |
| 5,282,824 A | 2/1994 | Gianturco |
| 5,287,861 A | 2/1994 | Wilk |
| 5,295,484 A | 3/1994 | Marcus et al. |
| 5,299,578 A | 4/1994 | Rotteveel et al. |
| 5,309,915 A | 5/1994 | Ember |
| 5,311,871 A | 5/1994 | Yock |
| 5,313,950 A | 5/1994 | Ishikawa et al. |
| 5,316,001 A | 5/1994 | Ferek-Petric et al. |
| 5,320,106 A | 6/1994 | Tanaka |
| 5,330,500 A | 7/1994 | Song |
| 5,334,183 A | 8/1994 | Wuchinich et al. |
| 5,334,210 A | 8/1994 | Gianturco |
| 5,339,289 A | 8/1994 | Erickson |
| 5,344,420 A | 9/1994 | Hilal et al. |
| 5,351,693 A | 10/1994 | Taimisto et al. |
| 5,363,852 A | 11/1994 | Sharkawy |
| 5,363,853 A | 11/1994 | Lieber et al. |
| 5,366,504 A | 11/1994 | Anderson et al. |
| 5,368,035 A | 11/1994 | Hamm et al. |
| 5,372,138 A | 12/1994 | Crowley et al. |
| 5,375,602 A | 12/1994 | Lancee et al. |
| 5,377,682 A | 1/1995 | Ueno et al. |
| 5,380,316 A | 1/1995 | Aita et al. |
| 5,381,795 A | 1/1995 | Nordgren et al. |
| 5,383,460 A | 1/1995 | Jang et al. |
| 5,383,887 A | 1/1995 | Nadal |
| 5,385,148 A | 1/1995 | Lesh et al. |
| 5,389,096 A | 2/1995 | Aita et al. |
| 5,402,792 A | 4/1995 | Kimura |
| 5,409,012 A | 4/1995 | Sahatjian |
| 5,409,019 A | 4/1995 | Wilk |
| 5,411,466 A | 5/1995 | Hess |
| 5,413,601 A | 5/1995 | Keshelava |
| 5,425,739 A | 6/1995 | Jessen |
| 5,427,107 A | 6/1995 | Milo et al. |
| 5,429,144 A | 7/1995 | Wilk |
| 5,435,314 A | 7/1995 | Dias |
| 5,443,498 A | 8/1995 | Fontaine |
| 5,443,843 A | 8/1995 | Curatolo et al. |
| 5,452,733 A | 9/1995 | Sterman et al. |
| 5,454,373 A | 10/1995 | Koger et al. |
| 5,454,809 A | 10/1995 | Janssen |
| 5,456,258 A | 10/1995 | Kondo et al. |
| 5,458,120 A | 10/1995 | Lorraine |
| 5,464,016 A | 11/1995 | Nicholas et al. |
| 5,465,726 A | 11/1995 | Dickinson et al. |
| 5,466,242 A | 11/1995 | Mori |
| 5,470,308 A | 11/1995 | Edwards et al. |
| 5,474,075 A | 12/1995 | Goldberg et al. |
| 5,484,416 A | 1/1996 | Gittings |
| 5,485,841 A | 1/1996 | Watkin et al. |
| 5,500,012 A | 3/1996 | Brucker et al. |
| 5,505,088 A | 4/1996 | Chandraratna et al. |
| 5,509,900 A * | 4/1996 | Kirkman ..................... 604/104 |
| 5,514,154 A | 5/1996 | Lau et al. |
| 5,520,684 A | 5/1996 | Imran |
| 5,522,822 A | 6/1996 | Phelps et al. |
| 5,524,630 A | 6/1996 | Crowley |
| 5,527,292 A | 6/1996 | Adams et al. |
| 5,527,324 A | 6/1996 | Krantz et al. |
| 5,540,713 A | 7/1996 | Schnepp-Pesch et al. |
| 5,545,195 A | 8/1996 | Lennox et al. |
| 5,545,210 A | 8/1996 | Hess et al. |
| 5,554,118 A | 9/1996 | Jang |
| 5,554,152 A | 9/1996 | Aita et al. |
| 5,555,886 A | 9/1996 | Weng et al. |
| 5,562,922 A * | 10/1996 | Lambert ..................... 424/486 |
| 5,564,434 A | 10/1996 | Halperin et al. |
| 5,571,086 A | 11/1996 | Kaplan et al. |

| | | | | | | |
|---|---|---|---|---|---|---|
| 5,571,180 | A | 11/1996 | Blom | 5,957,849 | A | 9/1999 | Munro |
| 5,573,531 | A | 11/1996 | Gregory | 5,957,919 | A | 9/1999 | Laufer |
| 5,575,815 | A | 11/1996 | Slepian et al. | 5,957,949 | A | 9/1999 | Leonhardt et al. |
| 5,575,818 | A | 11/1996 | Pinchuk | 5,957,974 | A | 9/1999 | Thompson et al. |
| 5,588,432 | A | 12/1996 | Crowley | 5,967,990 | A | 10/1999 | Thierman et al. |
| 5,593,417 | A | 1/1997 | Rhodes | 5,968,053 | A | 10/1999 | Revelas |
| 5,593,442 | A | 1/1997 | Klein | 5,968,070 | A | 10/1999 | Bley et al. |
| 5,596,989 | A | 1/1997 | Morita | 5,971,980 | A | 10/1999 | Sherman |
| 5,607,444 | A | 3/1997 | Lam | 5,972,017 | A | 10/1999 | Berg et al. |
| 5,615,679 | A | 4/1997 | Ri et al. | 5,976,178 | A | 11/1999 | Goldsteen et al. |
| 5,616,608 | A | 4/1997 | Kinsella et al. | 5,984,871 | A | 11/1999 | TenHoff et al. |
| 5,618,301 | A | 4/1997 | Hauenstein et al. | 5,989,276 | A | 11/1999 | Houser et al. |
| 5,630,837 | A | 5/1997 | Crowley | 5,993,484 | A | 11/1999 | Shmulewitz |
| D380,266 | S | 6/1997 | Boatman et al. | 6,003,517 | A | 11/1999 | Shmulewitz et al. |
| 5,645,559 | A | 7/1997 | Hachtman et al. | 6,001,124 | A | 12/1999 | Bachinski |
| 5,647,871 | A | 7/1997 | Levine et al. | 6,002,955 | A | 12/1999 | Willems et al. |
| 5,653,746 | A | 8/1997 | Schmitt | 6,004,269 | A | 12/1999 | Crowley et al. |
| 5,655,548 | A | 8/1997 | Nelson et al. | 6,004,273 | A | 12/1999 | Sakamoto et al. |
| 5,658,280 | A | 8/1997 | Issa | 6,004,319 | A | 12/1999 | Gobel et al. |
| 5,672,172 | A | 9/1997 | Zupkas | 6,007,544 | A | 12/1999 | Kim |
| 5,674,242 | A * | 10/1997 | Phan et al. ................ 606/198 | 6,007,574 | A | 12/1999 | Pulnev et al. |
| 5,674,277 | A | 10/1997 | Freitag | 6,010,529 | A | 1/2000 | Herweck et al. |
| 5,674,298 | A | 10/1997 | Levy et al. | 6,011,995 | A | 1/2000 | Guglielmi et al. |
| 5,678,555 | A | 10/1997 | O'Connell | 6,013,033 | A | 1/2000 | Berger et al. |
| 5,693,085 | A | 12/1997 | Buirge et al. | 6,013,093 | A | 1/2000 | Nott et al. |
| 5,704,361 | A | 1/1998 | Seward et al. | 6,013,854 | A | 1/2000 | Moriuchi |
| 5,713,949 | A | 2/1998 | Jayaraman | 6,015,405 | A | 1/2000 | Schwartz et al. |
| 5,716,393 | A | 2/1998 | Lindenberg et al. | 6,019,787 | A | 2/2000 | Richard et al. |
| 5,718,701 | A | 2/1998 | Shai et al. | 6,019,789 | A | 2/2000 | Dinh et al. |
| 5,720,735 | A | 2/1998 | Dorros | 6,022,371 | A | 2/2000 | Killion |
| 5,725,547 | A | 3/1998 | Chuter | 6,024,703 | A | 2/2000 | Zanelli et al. |
| 5,725,572 | A | 3/1998 | Lam et al. | 6,024,756 | A | 2/2000 | Huebsch et al. |
| 5,736,642 | A | 4/1998 | Yost et al. | 6,030,392 | A | 2/2000 | Dakov |
| 5,741,234 | A | 4/1998 | Aboul-Hosn | 6,032,674 | A | 3/2000 | Eggers et al. |
| 5,741,333 | A | 4/1998 | Frid | 6,036,702 | A | 3/2000 | Bachinski et al. |
| 5,746,767 | A | 5/1998 | Smith | 6,045,511 | A | 4/2000 | Ott et al. |
| 5,752,518 | A | 5/1998 | McGee et al. | 6,045,532 | A | 4/2000 | Eggers et al. |
| 5,755,769 | A | 5/1998 | Richard et al. | 6,048,362 | A | 4/2000 | Berg |
| 5,755,778 | A | 5/1998 | Kleshinski | 6,053,941 | A | 4/2000 | Lindenberg et al. |
| 5,759,769 | A | 6/1998 | Sia et al. | 6,059,731 | A | 5/2000 | Seward et al. |
| 5,762,638 | A | 6/1998 | Shikani et al. | 6,059,811 | A | 5/2000 | Pinchasik et al. |
| 5,779,642 | A | 7/1998 | Nightengale | 6,063,111 | A | 5/2000 | Hieshima et al. |
| 5,792,119 | A | 8/1998 | Marx | 6,064,902 | A | 5/2000 | Haissaguerre et al. |
| 5,795,325 | A | 8/1998 | Valley et al. | 6,066,169 | A | 5/2000 | McGuinness |
| 5,797,920 | A | 8/1998 | Kim | 6,068,638 | A | 5/2000 | Makower |
| 5,810,008 | A | 9/1998 | Dekel et al. | 6,070,094 | A | 5/2000 | Swanson et al. |
| 5,810,836 | A | 9/1998 | Hussein et al. | 6,074,349 | A | 6/2000 | Crowley |
| 5,824,046 | A | 10/1998 | Smith et al. | 6,074,416 | A | 6/2000 | Berg et al. |
| 5,824,048 | A | 10/1998 | Tuch | 6,080,109 | A | 6/2000 | Baker et al. |
| 5,830,191 | A | 11/1998 | Hildwein et al. | 6,096,053 | A | 8/2000 | Bates |
| 5,830,222 | A | 11/1998 | Makower | 6,099,563 | A * | 8/2000 | Zhong ................ 623/1.46 |
| 5,840,431 | A | 11/1998 | Kall | 6,112,123 | A | 8/2000 | Kelleher et al. |
| 5,843,158 | A | 12/1998 | Lenker et al. | 6,113,612 | A | 9/2000 | Swanson et al. |
| 5,843,175 | A | 12/1998 | Frantzen | 6,117,101 | A | 9/2000 | Diederich et al. |
| 5,849,037 | A | 12/1998 | Frid | 6,120,432 | A | 9/2000 | Sullivan et al. |
| 5,855,597 | A | 1/1999 | Jayaraman | 6,120,534 | A | 9/2000 | Ruiz |
| 5,855,598 | A * | 1/1999 | Pinchuk .................. 623/1.13 | 6,129,726 | A | 10/2000 | Edwards et al. |
| 5,860,951 | A | 1/1999 | Eggers et al. | 6,143,019 | A | 11/2000 | Motamedi et al. |
| 5,868,763 | A | 2/1999 | Spence et al. | 6,152,937 | A | 11/2000 | Peterson et al. |
| 5,868,777 | A | 2/1999 | Lam | 6,152,945 | A | 11/2000 | Bachinski et al. |
| 5,873,904 | A | 2/1999 | Ragheb et al. | 6,159,225 | A | 12/2000 | Makower |
| 5,876,345 | A | 3/1999 | Eaton et al. | 6,162,245 | A | 12/2000 | Jayaraman |
| 5,876,434 | A | 3/1999 | Flomenblit et al. | 6,165,127 | A | 12/2000 | Crowley |
| 5,876,445 | A | 3/1999 | Andersen et al. | 6,174,323 | B1 | 1/2001 | Biggs et al. |
| 5,876,448 | A | 3/1999 | Thompson et al. | 6,176,872 | B1 | 1/2001 | Miksza |
| 5,885,219 | A | 3/1999 | Nightengale | 6,183,444 | B1 | 2/2001 | Glines et al. |
| 5,916,158 | A | 6/1999 | Webster, Jr. | 6,186,942 | B1 | 2/2001 | Sullivan et al. |
| 5,921,995 | A | 7/1999 | Kleshinski | 6,190,353 | B1 | 2/2001 | Makower et al. |
| 5,922,019 | A | 7/1999 | Hankh et al. | 6,200,313 | B1 | 3/2001 | Abe et al. |
| 5,935,135 | A | 8/1999 | Bramfitt et al. | 6,200,564 | B1 | 3/2001 | Lamont et al. |
| 5,938,697 | A | 8/1999 | Killion et al. | 6,206,831 | B1 | 3/2001 | Suorsa et al. |
| 5,951,567 | A | 9/1999 | Javier, Jr. et al. | 6,231,587 | B1 | 5/2001 | Makower |
| 5,954,649 | A | 9/1999 | Chia et al. | 6,235,024 | B1 | 5/2001 | Tu |

| | | |
|---|---|---|
| 6,235,054 B1 | 5/2001 | Berg et al. |
| 6,241,742 B1 | 6/2001 | Spence et al. |
| 6,241,746 B1 | 6/2001 | Bosma et al. |
| 6,245,020 B1 | 6/2001 | Moore et al. |
| 6,245,057 B1 | 6/2001 | Sieben et al. |
| 6,245,102 B1 | 6/2001 | Jayaraman |
| 6,254,632 B1 | 7/2001 | Wu et al. |
| 6,258,100 B1 | 7/2001 | Alferness et al. |
| 6,258,115 B1 | 7/2001 | Dubrul |
| 6,261,601 B1 | 7/2001 | Talwar et al. |
| 6,264,690 B1 | 7/2001 | Von Oepen |
| 6,270,515 B1 | 8/2001 | Linden et al. |
| 6,270,524 B1 | 8/2001 | Kimura |
| 6,280,457 B1 | 8/2001 | Wallace et al. |
| 6,283,951 B1 | 9/2001 | Flaherty et al. |
| 6,283,983 B1 | 9/2001 | Makower et al. |
| 6,287,290 B1 | 9/2001 | Perkins et al. |
| 6,290,728 B1 | 9/2001 | Phelps et al. |
| 6,293,951 B1 | 9/2001 | Alferness et al. |
| 6,299,604 B1 * | 10/2001 | Ragheb et al. .............. 604/265 |
| 6,299,635 B1 | 10/2001 | Frantzen |
| 6,309,375 B1 | 10/2001 | Glines et al. |
| 6,309,415 B1 | 10/2001 | Pulnev et al. |
| 6,309,416 B1 | 10/2001 | Swanson et al. |
| 6,325,825 B1 | 12/2001 | Kula et al. |
| 6,328,689 B1 | 12/2001 | Gonzalez et al. |
| 6,334,869 B1 | 1/2002 | Leonhardt et al. |
| 6,335,029 B1 * | 1/2002 | Kamath et al. .............. 424/423 |
| 6,336,933 B1 | 1/2002 | Parodi |
| 6,342,591 B1 * | 1/2002 | Zamora et al. ................ 536/21 |
| 6,344,053 B1 | 2/2002 | Boneau |
| 6,355,057 B1 | 3/2002 | DeMarais et al. |
| 6,371,964 B1 | 4/2002 | Vargas et al. |
| 6,379,382 B1 * | 4/2002 | Yang .......................... 623/1.42 |
| 6,391,036 B1 | 5/2002 | Berg et al. |
| 6,394,093 B1 | 5/2002 | Lethi |
| 6,394,956 B1 | 5/2002 | Chandrasekaran et al. |
| 6,428,550 B1 | 8/2002 | Vargas et al. |
| 6,440,163 B1 | 8/2002 | Swanson et al. |
| 6,451,048 B1 | 9/2002 | Berg et al. |
| 6,458,153 B1 * | 10/2002 | Bailey et al. ................ 623/1.24 |
| 6,488,673 B1 | 12/2002 | Laufer et al. |
| 6,490,474 B1 | 12/2002 | Willis et al. |
| 6,506,408 B1 | 1/2003 | Palasis |
| 6,508,822 B1 | 1/2003 | Peterson et al. |
| 6,511,491 B2 | 1/2003 | Grudem et al. |
| 6,514,249 B1 | 2/2003 | Maguire |
| 6,514,290 B1 | 2/2003 | Loomas |
| 6,528,301 B1 | 3/2003 | Breme et al. |
| 6,533,812 B2 | 3/2003 | Swanson et al. |
| 6,585,655 B2 | 7/2003 | Crowley |
| 6,599,303 B1 | 7/2003 | Peterson et al. |
| 6,599,311 B1 | 7/2003 | Biggs et al. |
| 6,602,263 B1 | 8/2003 | Swanson et al. |
| 6,616,675 B1 | 9/2003 | Evard et al. |
| 6,620,176 B1 | 9/2003 | Peterson et al. |
| 6,629,951 B2 | 10/2003 | Laufer et al. |
| 6,634,363 B1 | 10/2003 | Danek et al. |
| 6,635,279 B2 | 10/2003 | Kolter et al. |
| 6,652,577 B2 | 11/2003 | Gianotti |
| 6,652,582 B1 | 11/2003 | Stinson |
| 6,660,015 B1 | 12/2003 | Berg et al. |
| 6,663,662 B2 | 12/2003 | Pacetti |
| 6,673,084 B1 | 1/2004 | Peterson et al. |
| 6,689,803 B2 | 2/2004 | Hunter |
| 6,692,494 B1 | 2/2004 | Cooper et al. |
| 6,699,256 B1 | 3/2004 | Logan et al. |
| 6,702,829 B2 | 3/2004 | Bachinski et al. |
| 6,712,804 B2 | 3/2004 | Roue et al. |
| 6,712,812 B2 | 3/2004 | Roschak et al. |
| 6,712,845 B2 | 3/2004 | Hossainy et al. |
| 6,719,781 B1 * | 4/2004 | Kim .......................... 623/1.13 |
| 6,730,064 B2 | 5/2004 | Ragheb et al. |
| 6,730,349 B2 | 5/2004 | Schwarz |
| 6,749,606 B2 | 6/2004 | Keast et al. |
| 6,770,070 B1 | 8/2004 | Balbierz |
| 6,790,228 B2 | 9/2004 | Hossainy et al. |
| 6,866,674 B2 | 3/2005 | Galdonik et al. |
| 6,869,443 B2 | 3/2005 | Buscemi et al. |
| 6,872,183 B2 | 3/2005 | Sampson et al. |
| 6,890,583 B2 | 5/2005 | Chudzik et al. |
| 6,899,731 B2 | 5/2005 | Li et al. |
| 6,918,869 B2 | 7/2005 | Shaw et al. |
| 6,918,927 B2 | 7/2005 | Bates et al. |
| 6,920,882 B2 | 7/2005 | Berg et al. |
| 6,941,950 B2 * | 9/2005 | Wilson et al. .......... 128/207.14 |
| 6,960,219 B2 | 11/2005 | Grudem et al. |
| 6,970,733 B2 | 11/2005 | Willis et al. |
| 6,994,713 B2 | 2/2006 | Berg et al. |
| 6,997,189 B2 | 2/2006 | Biggs et al. |
| 7,011,094 B2 | 3/2006 | Rapacki et al. |
| 7,014,654 B2 | 3/2006 | Welsh et al. |
| 7,022,088 B2 | 4/2006 | Keast et al. |
| 7,086,398 B2 | 8/2006 | Tanaka |
| 7,175,644 B2 | 2/2007 | Cooper et al. |
| 7,226,442 B2 | 6/2007 | Sheppard, Jr. et al. |
| 2001/0007940 A1 | 7/2001 | Hosheng et al. |
| 2001/0021872 A1 | 9/2001 | Bailey et al. |
| 2001/0044650 A1 | 11/2001 | Sismo et al. |
| 2001/0047180 A1 | 11/2001 | Grudem et al. |
| 2001/0052344 A1 | 12/2001 | Doshi |
| 2002/0002401 A1 | 1/2002 | McGuckin, Jr. et al. |
| 2002/0032477 A1 | 3/2002 | Helmus et al. |
| 2002/0042564 A1 | 4/2002 | Cooper et al. |
| 2002/0042565 A1 | 4/2002 | Cooper et al. |
| 2002/0049370 A1 | 4/2002 | Laufer et al. |
| 2002/0055772 A1 | 5/2002 | McGuckin, Jr. et al. |
| 2002/0071902 A1 | 6/2002 | Ding et al. |
| 2002/0091433 A1 | 7/2002 | Ding et al. |
| 2002/0111619 A1 | 8/2002 | Keast et al. |
| 2002/0111620 A1 | 8/2002 | Cooper et al. |
| 2002/0119178 A1 | 8/2002 | Levesque et al. |
| 2002/0128647 A1 | 9/2002 | Roschak |
| 2003/0017150 A1 | 1/2003 | Torphy |
| 2003/0070676 A1 | 4/2003 | Cooper et al. |
| 2003/0130657 A1 | 7/2003 | Tom et al. |
| 2003/0153971 A1 | 8/2003 | Chandraskearan |
| 2003/0216806 A1 | 11/2003 | Togawa et al. |
| 2004/0055606 A1 | 3/2004 | Hendricksen et al. |
| 2004/0060563 A1 | 4/2004 | Rapacki et al. |
| 2004/0073155 A1 | 4/2004 | Laufer et al. |
| 2004/0073201 A1 | 4/2004 | Cooper et al. |
| 2004/0073284 A1 | 4/2004 | Bates et al. |
| 2004/0093070 A1 | 5/2004 | Hojeibane et al. |
| 2004/0211434 A1 | 10/2004 | Loomas et al. |
| 2004/0220556 A1 | 11/2004 | Cooper et al. |
| 2004/0261203 A1 | 12/2004 | Dworzan |
| 2005/0043751 A1 | 2/2005 | Phan et al. |
| 2005/0043752 A1 | 2/2005 | Phan et al. |
| 2005/0049615 A1 | 3/2005 | Cooper et al. |
| 2005/0056292 A1 | 3/2005 | Cooper |
| 2005/0060041 A1 | 3/2005 | Phan et al. |
| 2005/0060042 A1 | 3/2005 | Phan et al. |
| 2005/0060044 A1 | 3/2005 | Roschak |
| 2005/0085801 A1 | 4/2005 | Cooper et al. |
| 2005/0096529 A1 | 5/2005 | Cooper et al. |
| 2005/0107783 A1 | 5/2005 | Tom et al. |
| 2005/0137518 A1 | 6/2005 | Biggs et al. |
| 2005/0137611 A1 | 6/2005 | Escudero et al. |
| 2005/0137712 A1 | 6/2005 | Biggs et al. |
| 2005/0137715 A1 | 6/2005 | Phan et al. |

| | | | | | |
|---|---|---|---|---|---|
| 2005/0177144 A1* | 8/2005 | Phan et al. .................... 606/14 | 2006/0142672 A1 | 6/2006 | Keast et al. |
| 2005/0192526 A1 | 9/2005 | Biggs et al. | 2006/0276807 A1 | 12/2006 | Keast et al. |
| 2005/0228268 A1 | 10/2005 | Cole | 2006/0280772 A1 | 12/2006 | Roschak et al. |
| 2006/0116749 A1 | 6/2006 | Willink et al. | 2006/0280773 A1 | 12/2006 | Roschak et al. |
| 2006/0135984 A1 | 6/2006 | Kramer et al. | 2007/0123922 A1 | 5/2007 | Cooper et al. |

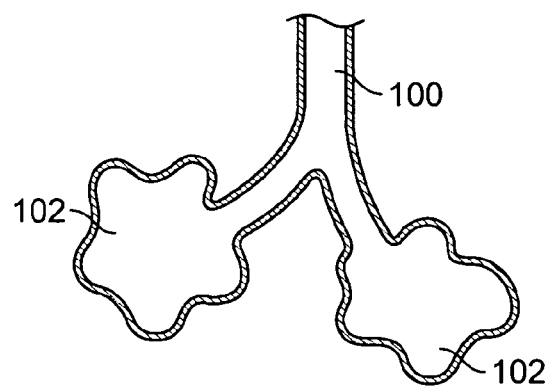
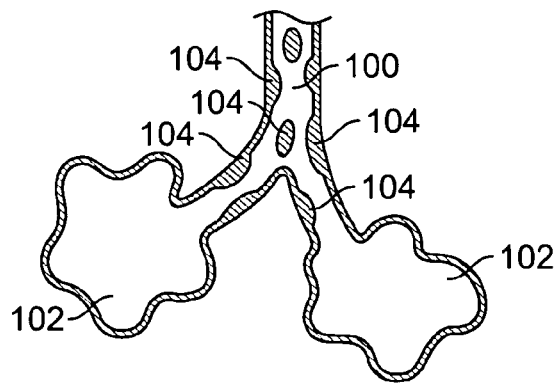
FIG. 1A    FIG. 1B
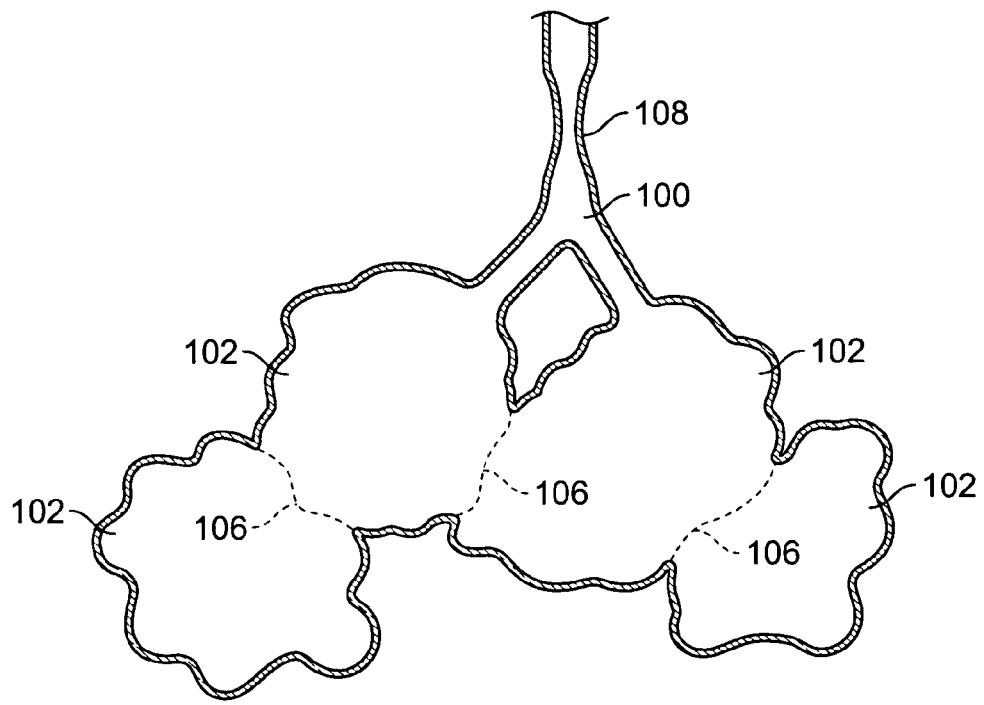
FIG. 1C

ANTIPROLIFERATIVE DEVICES FOR MAINTAINING PATENCY OF SURGICALLY CREATED CHANNELS IN A BODY ORGAN

CROSS-REFERENCE TO RELATED APPLICATIONS

This application is a continuation-in-part of U.S. patent application Ser. No. 10/235,240 filed on Sep. 4, 2002 which is a non-provisional of U.S. provisional application No. 60/317,338 filed on Sep. 4, 2001. This application is also a continuation-in-part of U.S. patent application Ser. No. 10/458,085, filed Jun. 9, 2003. The entirety of each of the above are hereby incorporated by reference.

BACKGROUND OF THE INVENTION

The American Lung Association (ALA) estimates that nearly 16 million Americans suffer from chronic obstructive pulmonary disease (COPD) which includes diseases such as chronic bronchitis, emphysema, and some types of asthma. The ALA estimated that COPD was the fourth-ranking cause of death in the U.S. The ALA estimates that about 14 million and 2 million Americans suffer from emphysema and chronic bronchitis respectively.

Those inflicted with COPD face disabilities due to the limited pulmonary functions. Usually, individuals afflicted by COPD also face loss in muscle strength and an inability to perform common daily activities. Often, those patients desiring treatment for COPD seek a physician at a point where the disease is advanced. Since the damage to the lungs is irreversible, there is little hope of recovery. Most times, the physician cannot reverse the effects of the disease but can only offer treatment and advice to halt the progression of the disease.

To understand the detrimental effects of COPD, the workings of the lungs requires a cursory discussion. The primary function of the lungs is to permit the exchange of two gasses by removing carbon dioxide from arterial blood and replacing it with oxygen. Thus, to facilitate this exchange, the lungs provide a blood gas interface. The oxygen and carbon dioxide move between the gas (air) and blood by diffusion. This diffusion is possible since the blood is delivered to one side of the blood-gas interface via small blood vessels (capillaries). The capillaries are wrapped around numerous air sacs called alveoli which function as the blood-gas interface. A typical human lung contains about 300 million alveoli.

The air is brought to the other side of this blood-gas interface by a natural respiratory airway, hereafter referred to as a natural airway or airway, consisting of branching tubes which become narrower, shorter, and more numerous as they penetrate deeper into the lung. Specifically, the airway begins with the trachea which branches into the left and right bronchi which divide into lobar, then segmental bronchi. Ultimately, the branching continues down to the terminal bronchioles which lead to the alveoli. Plates of cartilage may be found as part of the walls throughout most of the airway from the trachea to the bronchi. The cartilage plates become less prevalent as the airways branch. Eventually, in the last generations of the bronchi, the cartilage plates are found only at the branching points. The bronchi and bronchioles may be distinguished as the bronchi lie proximal to the last plate of cartilage found along the airway, while the bronchiole lies distal to the last plate of cartilage. The bronchioles are the smallest airways that do not contain alveoli. The function of the bronchi and bronchioles is to provide conducting airways that lead air to and from the gas-blood interface. However, these conducting airways do not take part in gas exchange because they do not contain alveoli. Rather, the gas exchange takes place in the alveoli which are found in the distal most end of the airways.

The mechanics of breathing include the lungs, the rib cage, the diaphragm and abdominal wall. During inspiration, inspiratory muscles contract increasing the volume of the chest cavity. As a result of the expansion of the chest cavity, the pleural pressure, the pressure within the chest cavity, becomes sub-atmospheric. Consequently, air flows into the lungs and the lungs expand. During unforced expiration, the inspiratory muscles relax and the lungs begin to recoil and reduce in size. The lungs recoil because they contain elastic fibers that allow for expansion, as the lungs inflate, and relaxation, as the lungs deflate, with each breath. This characteristic is called elastic recoil. The recoil of the lungs causes alveolar pressure to exceed atmospheric pressure causing air to flow out of the lungs and deflate the lungs. If the lungs' ability to recoil is damaged, the lungs cannot contract and reduce in size from their inflated state. As a result, the lungs cannot evacuate all of the inspired air.

In addition to elastic recoil, the lung's elastic fibers also assist in keeping small airways open during the exhalation cycle. This effect is also known as "tethering" of the airways. Tethering is desirable since small airways do not contain cartilage that would otherwise provide structural rigidity for these airways. Without tethering, and in the absence of structural rigidity, the small airways collapse during exhalation and prevent air from exiting thereby trapping air within the lung.

Emphysema is characterized by irreversible biochemical destruction of the alveolar walls that contain the elastic fibers, called elastin, described above. The destruction of the alveolar walls results in a dual problem of reduction of elastic recoil and the loss of tethering of the airways. Unfortunately for the individual suffering from emphysema, these two problems combine to result in extreme hyperinflation (air trapping) of the lung and an inability of the person to exhale. In this situation, the individual will be debilitated since the lungs are unable to perform gas exchange at a satisfactory rate.

One further aspect of alveolar wall destruction is that the airflow between neighboring air sacs, known as collateral ventilation or collateral air flow, is markedly increased as when compared to a healthy lung. While alveolar wall destruction decreases resistance to collateral ventilation, the resulting increased collateral ventilation does not benefit the individual since air is still unable to flow into and out of the lungs. Hence, because this trapped air is rich in $CO_2$, it is of little or no benefit to the individual.

Chronic bronchitis is characterized by excessive mucus production in the bronchial tree. Usually there is a general increase in bulk (hypertrophy) of the large bronchi and chronic inflammatory changes in the small airways. Excessive amounts of mucus are found in the airways and semisolid plugs of this mucus may occlude some small bronchi. Also, the small airways are usually narrowed and show inflammatory changes.

Currently, although there is no cure for COPD, treatment includes bronchodilator drugs, and lung reduction surgery. The bronchodilator drugs relax and widen the air passages thereby reducing the residual volume and increasing gas flow permitting more oxygen to enter the lungs. Yet, bronchodilator drugs are only effective for a short period of time and require repeated application. Moreover, the bronchodilator drugs are only effective in a certain percentage of the population of those diagnosed with COPD. In some cases, patients suffering from COPD are given supplemental oxygen to assist in breathing. Unfortunately, aside from the impracticalities of needing to maintain and transport a source of oxygen for everyday activities, the oxygen is only partially functional and does not eliminate the effects of the COPD. Moreover, patients requiring a supplemental source of oxygen are usually never able to return to functioning without the oxygen.

Lung volume reduction surgery is a procedure which removes portions of the lung that are over-inflated. The portion of the lung that remains has relatively better elastic recoil, providing reduced airway obstruction. The reduced lung volume also improves the efficiency of the respiratory muscles. However, lung reduction surgery is an extremely traumatic procedure which involves opening the chest and thoracic cavity to remove a portion of the lung. As such, the procedure involves an extended recovery period. Hence, the long term benefits of this surgery are still being evaluated. In any case, it is thought that lung reduction surgery is sought in those cases of emphysema where only a portion of the lung is emphysematous as opposed to the case where the entire lung is emphysematous. In cases where the lung is only partially emphysematous, removal of a portion of emphysematous lung which was compressing healthier portions of the lung allows the healthier portions to expand, increasing the overall efficiency of the lung. If the entire lung is emphysematous, however, removal of a portion of the lung removes gas exchanging alveolar surfaces, reducing the overall efficiency of the lung. Lung volume reduction surgery is thus not a practical solution for treatment of emphysema where the entire lung is diseased. Moreover, conventional lung volume reduction surgery is an open surgical procedure which carries the risk of surgical complications and requires a significant period of time for recuperation.

Both bronchodilator drugs and lung reduction surgery fail to capitalize on the increased collateral ventilation taking place in the diseased lung. There remains a need for a medical procedure that can alleviate some of the problems caused by COPD. There is also a need for a medical procedure that alleviates some of the problems caused by COPD irrespective of whether a portion of the lung, or the entire lung is emphysematous. The production and maintenance of collateral openings through an airway wall allows air to pass directly out of the lung tissue responsible for gas exchange. These collateral openings serve to decompress hyperinflated lungs and/or facilitate an exchange of oxygen into the blood.

Methods and devices for creating and maintaining collateral channels are discussed in U.S. patent application Ser. No. 09/633,651, filed on Aug. 7, 2000; U.S. patent application Ser. Nos. 09/947,144, 09/946,706, and 09/947,126 all filed on Sep. 4, 2001; U.S. Provisional Application No. 60/317,338 filed on Sep. 4, 2001; U.S. Provisional Application No. 60/334,642 filed on Nov. 29, 2001; U.S. Provisional Application No. 60/367,436 filed on Mar. 20, 2002; and U.S. Provisional Application No. 60/374,022 filed on Apr. 19, 2002 each of which is incorporated by reference herein in its entirety.

Although creating an opening through an airway wall may overcome the shortcomings associated with bronchodilator drugs and lung volume reduction surgery, various problems can still arise. When a hole is surgically created in tissue the healing cascade is triggered. This process is characterized by an orderly sequence of events, which can be broadly classified into distinct phases. These phases proceed in a systematic fashion, with a high degree of integration, organization, and control. However, the various stages are not sharply delineated, but overlap considerably, and factors affecting one phase have a stimulatory or inhibitory effect on the overall process.

The result of this wound healing process is tissue proliferation that can occlude or otherwise close the surgically created opening. Additionally, in the event an implant is deployed in the surgically created opening to maintain the patency of the opening, the implant may become encapsulated or filled with tissue thereby occluding the channel.

Drug eluting coronary-type stents are not known to overcome the above mentioned events because these stents are often substantially cylindrical (or otherwise have a shape that conforms to the shape of a tubular blood vessel). Hence, they may slide and eject from surgically created openings in an airway wall leading to rapid closure of any channel. Additionally, the design and structure of the coronary-type stents reflect the fact that these stents operate in an environment that contains different tissues when compared to the airways not to mention an environment where there is a constant flow of blood against the stent. Moreover, the design of coronary stents also acknowledges the need to place the stent within a tubular vessel and avoid partial restenosis of the vessel after stent placement so that blood may continue to flow. In view of the above, implants suited for placement in the coronary are often designed to account for factors that may be insignificant when considering a device for the airways.

Not surprisingly, experiments in animal models found that placement of coronary drug eluting stents (i.e., paclitaxel drug eluting vascular stents and sirolimus drug eluting stents) into the airway openings did not yield positive results in maintaining the patency of the opening. The shortcomings were both in the physical structure of the stent which did not lend itself to the airways as well as the inability of those drug eluting devices to control the healing cascade caused by creation of the channel. The majority of these devices filled with tissue at an early stage and an inspection of the remainder of the implanted devices indicated imminent closure.

An understanding of the distinctions between the healing response in the coronary versus the airways may explain this outcome. For purposes of our discussion, the healing response in both the coronary and the lungs may be divided into approximately four stages as measured relative to the time of the injury: 1) acute phase; 2) sub-chronic phase; 3) chronic phase; and 4) late phase.

In the coronary, after trauma caused by the placement of a coronary stent, the healing process begins in the acute phase with thrombus and acute inflammation. During the sub-chronic phase, there is an organization of the thrombus, an acute/chronic inflammation and early neointima hyperplasia. In the following chronic phase, there is a proliferation of smooth muscle cells along with chronic inflammation and adventitial thickening. In the late stage of the healing process there is chronic inflammation, neointimal remodeling, medial hypertrophy and adventitial thickening.

Based upon the observations in a rabbit model, the healing response in the airway begins with a fibrinous clot, edema hemorrhage, and fibrin deposition. In the sub-chronic phase there is re-epithelialization, mucosal hypertrophy, squamous metaplasia, fibroplasias and fibrosis. In the chronic phase, while the epithelium is intact and there is less mucosal hypertrophy, there is still fibroplasia and fibrosis. In the late stage the respiratory epithelium is intact and there is evidence of a scar.

Accordingly, the unique requirements of the airways and collateral channels calls for specific features for any implant used in collateral channels. For example, these implants/conduits are often placed across three different tissue zones; namely the parenchyma, the newly sectioned airway wall, and the interior of the airway surface. Each different zone may have a different reaction to the presence of the implant/ conduit. The parenchyma may build up a layer of scar tissue around the conduit, which may eventually eject the implant or block the air path on the parenchyma side of the conduit. The airway wall may undergo a healing response as a result of the trauma of the procedure. This healing response and associated tissue growth may restrict air-flow through the implant. Furthermore, mucus from the airways may deposit in to the conduit thereby further occluding the conduit.

In addition, placement of an implant or conduit within the collateral channel may present additional structure requirements for the devices. For example, surgeons often use radiological imaging to place coronary stents within the vasculature. In most cases, placement of coronary stents is critical so that the ends of the coronary stent straddle the vascular obstruction. In contrast, a surgeon placing an implant in collateral channels is often using a remote access device such as a bronchoscope or endoscope that allows for direct observation of the device during placement. For proper placement of the implant, and in cases where it is important to "sandwich" the airway wall, it is necessary to identify the center and/or edges of the conduit or implant prior to expansion of the device. It follows that failure to properly place the implant may result in detachment of the implant (via insufficient attachment to the airway wall), pneumothorax (if the implant is advanced too distally and breaches the pleural cavity), or deployment of the implant wholly in the lung parenchyma exterior to the airway wall. Accordingly, such devices may require a visual indicator to assist the medical practitioner during placement and to offer a measure of safety so that the device is not improperly advanced/deployed thus creating additional complications.

Accordingly, there remains a need for devices and methods that specifically address the requirements discussed herein.

BRIEF SUMMARY OF THE INVENTION

The devices and methods described herein serve to maintain the patency of a channel surgically created in an organ such as an airway wall. In particular, the devices and methods are suited for placement within a channel created within the airway wall and prevent closure of the channel such that air may flow through the channel and into the airway.

It is noted that the devices and methods described herein have particular use for individuals having emphysema and COPD. However, the devices and methods could also benefit any individuals having hyperinflation of the lungs.

Delivery devices for delivering the implants and/or creating the opening are described in U.S. Provisional Application No. 60/488,332, filed Jul. 18, 2003, and U.S. patent application Ser. No. 10/894,876 (U.S. 2005/0056292A1) entitled DEVICES FOR MAINTAINING PATENCY OF SURGICALLY CREATED CHANNELS IN TISSUE, and filed on Jul. 19, 2004, the entirety of both are herein incorporated by reference.

Implants of the present invention may include a support member having a structure that is adapted for placement within a wall of a body organ, especially an airway wall.

When used in the lungs implants of the present invention modify the healing response of the lung tissue (e.g., at the site of newly created hole/channel) for a sufficient time until the healing response of the lung tissue subsides or reduces such that the hole/channel becomes a persistent air path. For example, the implant and bioactive substance will modify the healing response for a sufficient time until the healing response is reduced and, from a visual observation, the body treats the opening essentially as a natural airway passage rather than as an injury to the airway wall.

Variations of the invention include implants having compositions comprising a polymer which either serves as a carrier for the agent or as a delivery barrier for the agent. In those variations of the implant used in the airways, the composition may provide a steady release rate of bio-active substance as well as have a sufficient amount of available bio-active substance to modify the healing response of the lung tissue. As described herein, such a delivery system takes advantage of the tissue environment surrounding the airways.

The antiproliferative agent of the present invention is one that modifies a healing response. Various agents are discussed below, examples include a microtubule stabilizing agent such as taxol or paclitaxel, or a microtubule destabilizing agent such as vincristine, vinblastine, podophylotoxin, estramustine, noscapine, griseofulvin, dicoumarol, a vinca alkaloid, or a combination thereof. Furthermore, the agent may include steroids, non-steroidal anti-inflammatories, rapamycin, dactinomycin, sirolimus, everolimus, Abt-578, tacrolimus, and a combination thereof. It is noted that the composition or implant may also include additional substance as required by the location of the implant. Such substances may affect/suppress mucus production, provide protection against bacteria, or maintain sterility of the implant site or surrounding tissue. It is contemplated that the bio-active substances listed herein includes all forms of the substances (e.g., analogs, derivatives, salt forms and crystalline forms.)

Variations of the invention also may include visualization features which provide assistance when attempting to place the implant from within an organ and having no or little direct visibility outside of the organ.

The invention may also include additional features such as valves within the implant to regulate flow or provide a protective barrier.

It is contemplated that though the invention includes a combination of support member and bioactive substance, it is noted that the structural configurations of several, if not all, of the support members provide unique advantages that lend themselves to use in securing the implant about a wall of an organ. Therefore, it is further contemplated that the structural configurations may also provide inventive embodiments without the bioactive substance.

This application is also related to the following application 60/420,440 filed Oct. 21, 2002; 60/387,163 filed Jun. 7, 2002; Ser. No. 10/235,240 filed Sep. 4, 2002; Ser. No. 09/947,144 filed Sep. 4, 2001; Ser. No. 09/908,177 filed Jul. 18, 2001; Ser. No. 09/633,651 filed Aug. 7, 2000; and 60/176,141 filed Jan. 14, 2000; Ser. No. 10/080,344 filed Feb. 21, 2002; Ser. No. 10/079,605 filed Feb. 21, 2002; and Ser. No. 10/280,851 filed Oct. 25, 2002. Each of which is incorporated by reference herein. Accordingly, where not inconsistent with the principles described herein, features and aspects of the invention may be combined with the various implants and conduits described in the above related applications.

BRIEF DESCRIPTION THE DRAWINGS

FIGS. 1A-1C illustrate various states of the natural airways and the blood-gas interface.

Figure 3A:
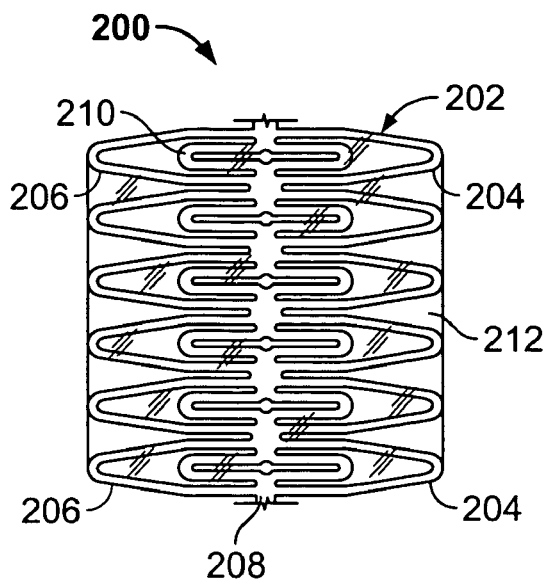
Figure 3B:
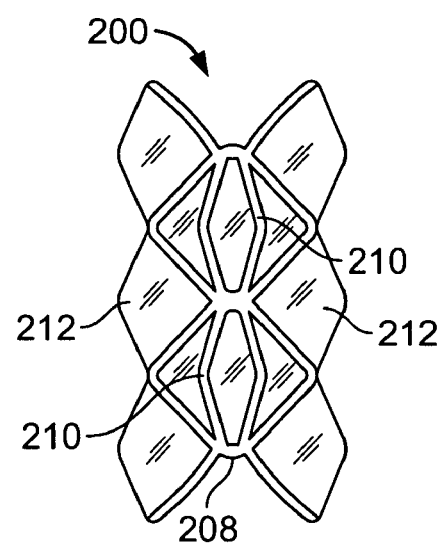
Figure 3C:
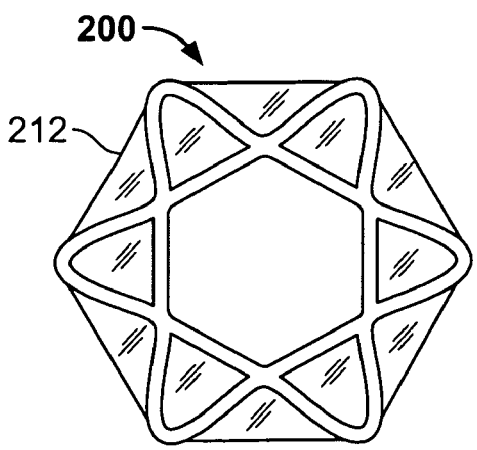

FIGS. 3A-3C provide various views of a variation of an implant of the present invention.

Figure 4A:
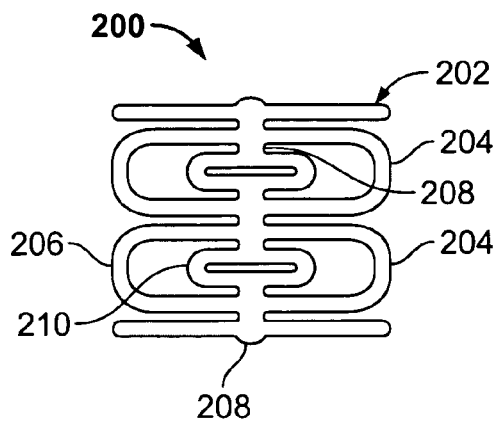
Figure 4B:
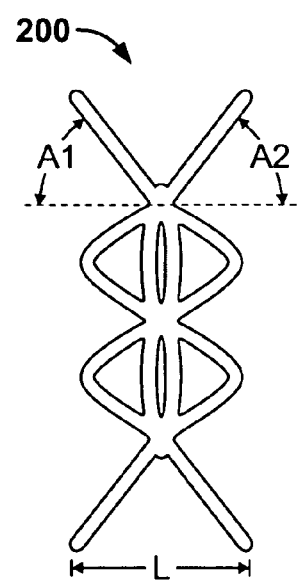
Figure 4C:
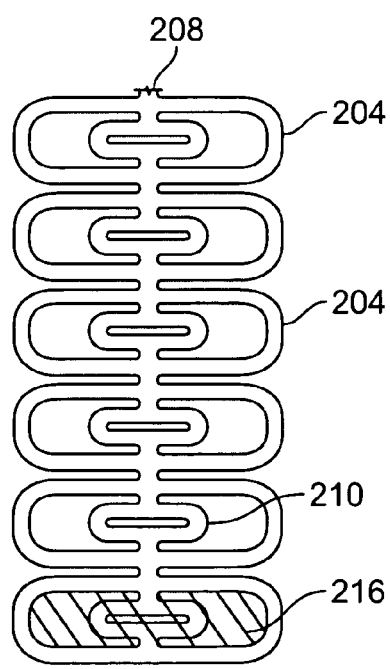

FIGS. 4A-4C are views of an additional variation of the invention.

FIGS. 5A-5C and 6A-6B illustrate a variation of the invention having control members in an alternating fashion about the implant and additional control members at an end of the implant.

Figure 7A:
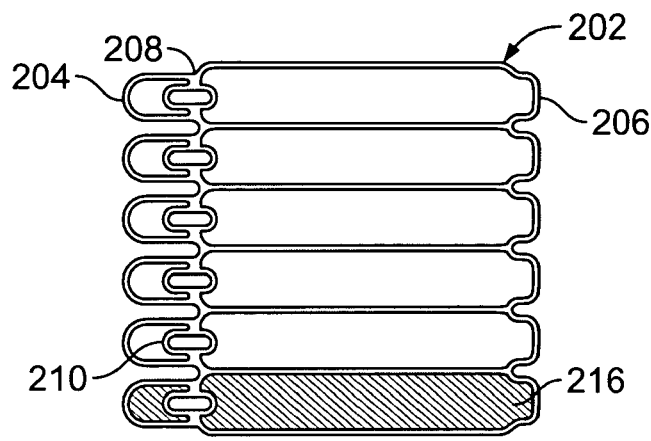
Figure 7B:
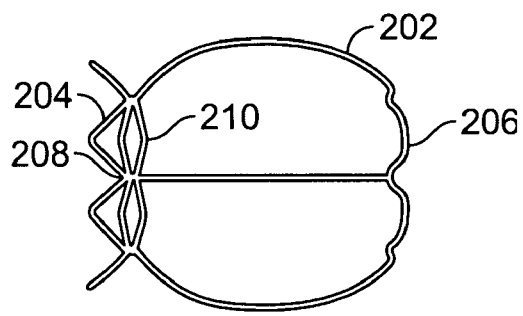
Figure 7C:
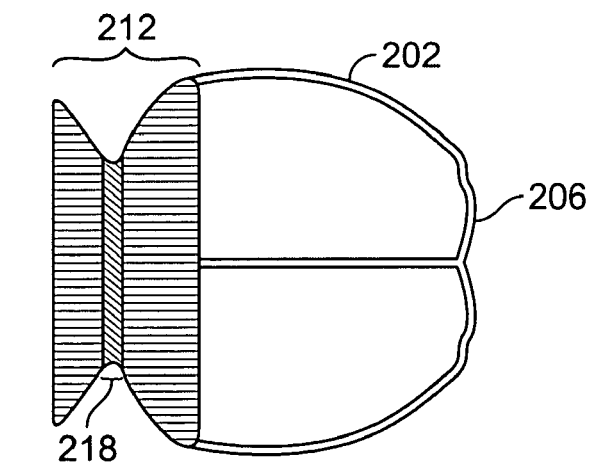

FIGS. 7A-7C illustrate a variation of the invention where the proximal portion and the distal portion are of differing sizes.

Figure 8A:
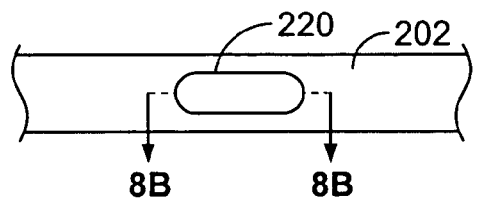
Figure 8B:
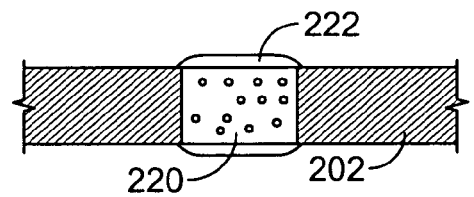

FIGS. 8A-8B illustrate additional variations of delivering an bioactive agent with the present invention.

Figure 9A:
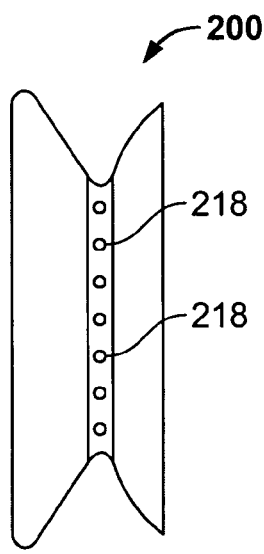
Figure 9B:
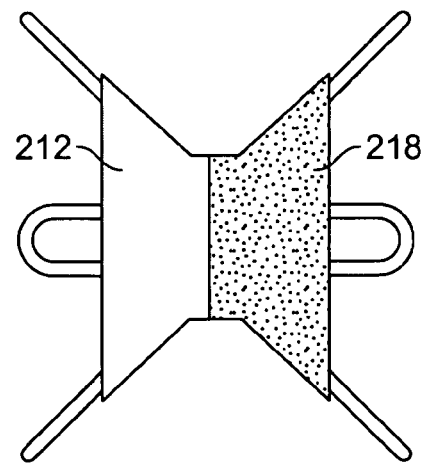
Figure 9C:
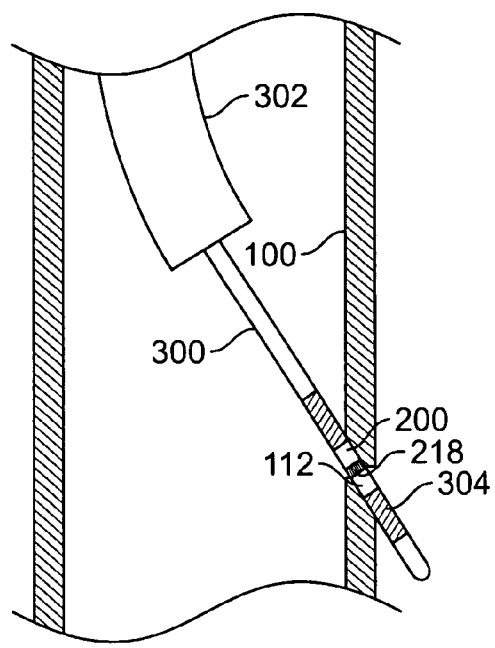

FIGS. 9A-9C illustrate variations of the present invention having visualization marks or features.

Figure 10A:
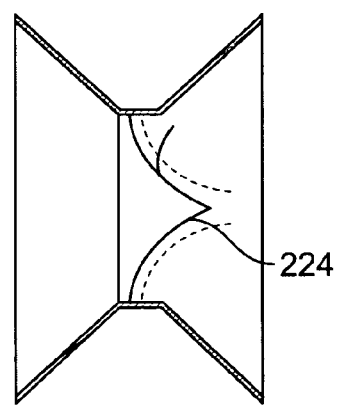
Figure 10B:
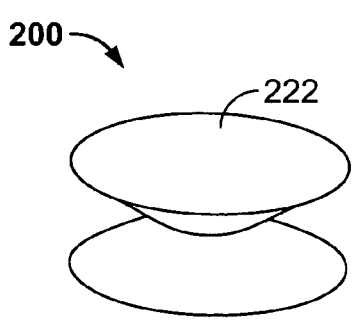

FIG. 10A-10B illustrate variations of the invention having valves and barriers within the device.

Figure 11A:
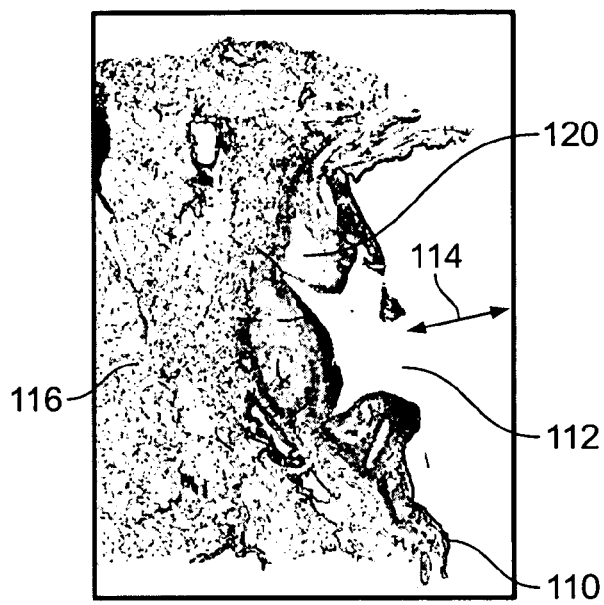
Figure 11B:
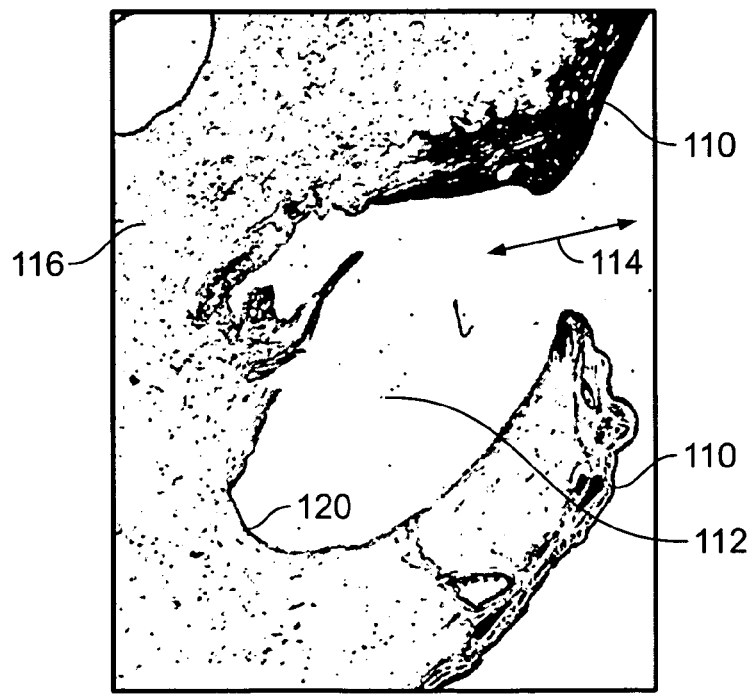

FIG. 11A-11B illustrate histology samples comparing conventional devices and an implant of the present invention.

Figure 12:
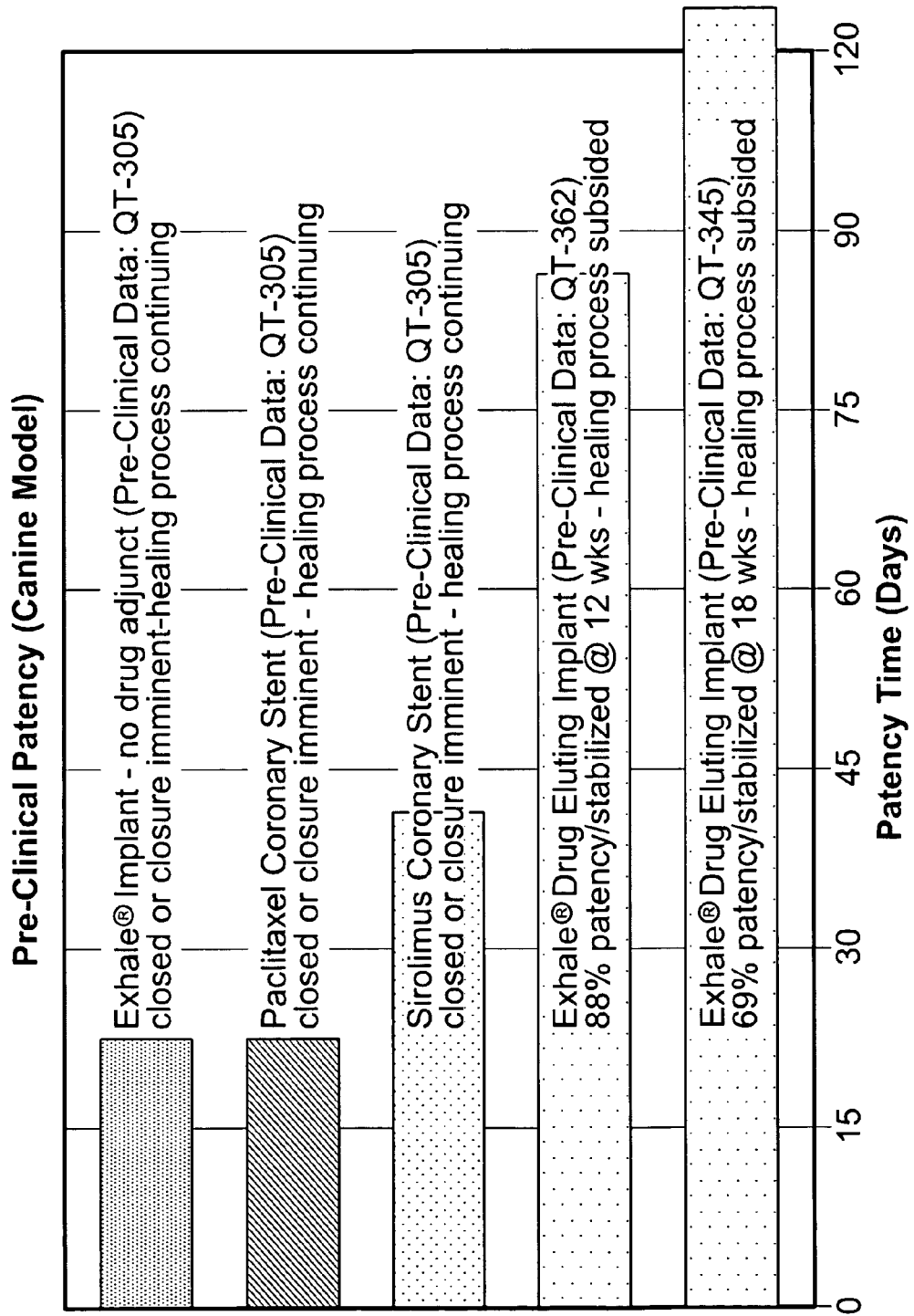

FIG. 12 illustrates pre-clinical data of an animal model comparing conventional devices, coronary drug eluting stents, and implants of the present invention.

DETAILED DESCRIPTION

Described herein are devices (and methods) for improving the gas exchange in the lung. In particular, methods and devices are described that serve to maintain and extend the patency of collateral openings or channels through an airway wall so that air is able to pass directly out of the lung tissue and into the airways. This facilitates exchange of oxygen into the blood and decompresses hyper inflated lungs.

By "channel" it is meant to include, but not be limited to, any opening, hole, slit, channel or passage created in the tissue wall (e.g., airway wall). The channel may be created in tissue having a discrete wall thickness and the channel may extend all the way through the wall. Also, a channel may extend through lung tissue which does not have well defined boundaries such as, for example, parenchymal tissue.

FIGS. 1A-1C are simplified illustrations of various states of a natural airway and a blood gas interface found at a distal end of those airways. FIG. 1A shows a natural airway 100 which eventually branches to a blood gas interface 102.

Although not shown, the airway comprises an internal layer of epithelial pseudostratified columnar or cuboidal cells. Mucous secreting goblet cells are also found in this layer and cilia may be present on the free surface of the epithelial lining of the upper respiratory airways. Supporting the epithelium is a loose fibrous, glandular, vascular lamina propria including mobile fibroblasts. Deep in this connective tissue layer is supportive cartilage for the bronchi and smooth muscle for the bronchi and bronchioles.

FIG. 1B illustrates an airway 100 and blood gas interface 102 in an individual having COPD. The obstructions 104 impair the passage of gas between the airways 100 and the interface 102. FIG. 1C illustrates a portion of an emphysematous lung where the blood gas interface 102 expands due to the loss of the interface walls 106 which have deteriorated due to a bio-chemical breakdown of the walls 106. Also depicted is a constriction 108 of the airway 100. It is generally understood that there is usually a combination of the phenomena depicted in FIGS. 1A-1C. Often, the states of the lung depicted in FIGS. 1B and 1C may be found in the same lung.

Figure 1D:
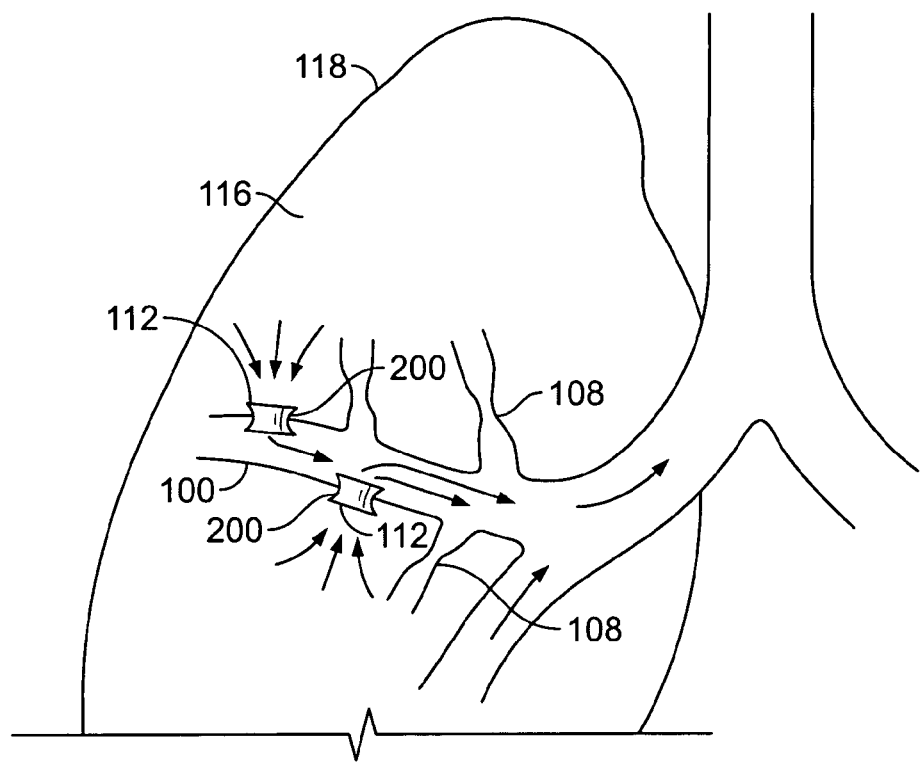
FIG. 1D illustrates a schematic of a lung demonstrating a principle of the invention described herein.

FIG. 1D illustrates airflow in a lung 118 when implants 200 are placed in collateral channels 112. As shown, collateral channels 112 (located in an airway wall) place lung tissue parenchyma 116 in fluid communication with airways 100 allowing air to pass directly out of the airways 100 whereas constricted airways 108 may ordinarily prevent air from exiting the lung tissue parenchyma 116. While the invention is not limited to the number of collateral channels which may be created, it is to be understood that 1 or 2 channels may be placed per lobe of the lung and perhaps, 2-12 channels per individual patient. However, as stated above, the invention includes the creation of any number of collateral channels in the lung. This number may vary on a case by case basis. For instance, in some cases in an emphysematous lung, it may be desirable to place 3 or more collateral channels in one or more lobes of the lung.

Figure 2A:
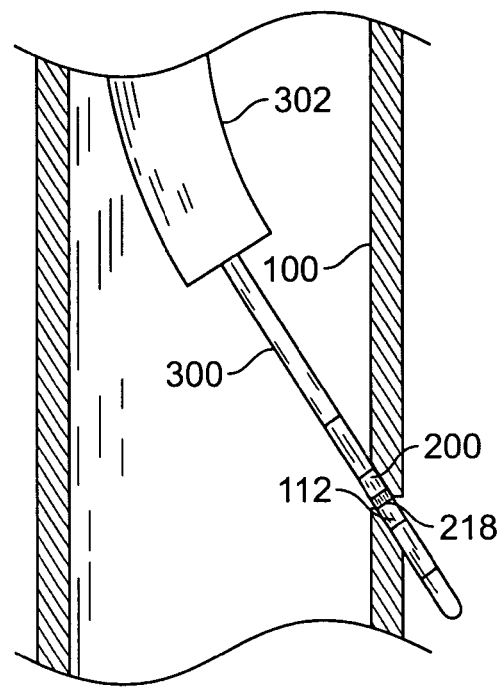
FIGS. 2A-2B illustrates deployment of an implant of the present invention.
Figure 2B:
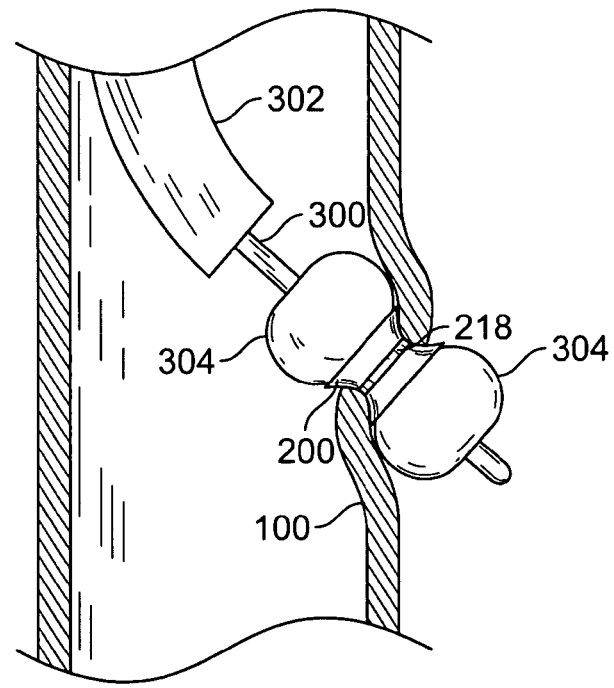

FIGS. 2A-2B illustrate deployment of a variation of an implant 200 of the present invention. As discussed herein, the implant 200 is well suited for maintaining an opening in a wall of a body organ. In this example, the illustration depicts the implant 200 as deployed into a collateral channel 112 formed in a wall of an airway 100. Referring to FIG. 2A, a delivery device 300 carrying the implant 200 is advanced to the site and inserted into the channel 112. The delivery device 300 may optionally be constructed to also form the channel 112. Furthermore, the delivery device 300 may extend from an access device such as an endoscope or bronchoscope 302, or it may be directly advanced to the site.

FIG. 2B illustrates deployment of the implant 200 in the airway wall 100. As shown, an expandable member, such as a balloon 304, expands the implant 200 into a non-cylindrical shape that is able to sandwich or capture the tissue 100 between the expanded portions of the implant 200. In some variations of the invention, the implant 200 forms a non-cylindrical (e.g., a "grommet" or "hour-glass") shape that is suited, when used in the airways, for limiting movement of the implant 200 within the tissue opening and securing the implant 200 about the perimeter of the tissue opening in the airway wall. For example, the implant 200 expands in the mid portion and flares at the ends to retain itself within the opening in the airway wall. Also, as illustrated, the grommet shape of the implant 200 extends only minimally into the airway.

As noted above, the implant is suited for placement about an opening in the wall of an organ. In some cases, the implant is suited to placement in an organ having a thin wall. Through observation, applicants noted that airway wall thickness is fairly proportional to the diameter of the airway lumen by approximately a factor of ⅙. While the invention is not limited to use in any particular sized airway, on average the implant is placed in airways ranging from 3 mm to 15 mm in diameter with respective airway wall thicknesses of 0.5 mm to 2.5 mm. Therefore, in many variations of the invention, the grommet or hour-glass shape will be suitable to retain itself on the relatively thin airway wall tissue. In forming this shape, a variation of the implant 200 shrinks in axial length as it secures itself within the channel. Shrinking in axial length may also provide additional benefit as it reduces the length of the implant 200 that extends into the airway. This reduction in length may prevent unwanted tissue damage to the airway wall and/or occlusion of the airway.

In additional variations of the invention, the implant 200 must not only capture relatively thin tissue, but must also maintain a minimum internal diameter to allow sufficient air flow. For example, a fewer number of implants may be used given a sufficiently large diameter. In such cases it is undesirable for the implant 200 to constrict in internal diameter as it forms the non-cylindrical shape. In other variations, the entire implant is expandable, but a portion of the implant 200 expands to a greater amount as compared to a remainder of the implant. Such a configuration allows for the entire implant 200 to expand while still forming a non-cylindrical shape.

As described below, the implants of the present invention include a support member and a composition that maintain patency of the channel. Variations of the invention include support members selected from a mesh or woven structure either of which are comprised of a metal alloy (e.g., stainless steel, titanium, a shape-memory alloy, etc.), a polymer, a ceramic, or a combination thereof. The support member provides a structure that mechanically maintains patency of the channel as well as provides a delivery means for the composition or other substances as described herein. It is specifically noted that while the variations of the present invention are suited for use in the airways, the invention is not limited to such applications. Rather, the variations of the present invention may be used in various applications as appropriate.

FIG. 3A illustrates a planar view of a variation of an implant 200 where the support member 202 is in the unexpanded shape. In this variation, the support member 202 comprises a plurality of struts or members and has a proximal portion 204, a distal portion 206, and a mid-portion 208 therebetween.

A composition 212, as described herein, is located on the implant. The composition 212 may encapsulate the support member 202, or it may be located on an exterior or interior surface. Alternatively, it may be located between or within the intensities of the support member 202. FIG. 3A also illustrates the struts or members (i.e., the extension member) on the proximal and distal portions 204, 206 as being tapered. Because the proximal and distal portions 204, 206 expand significantly, there is a propensity for the composition to tear at these locations. The tapering configuration is helpful to prevent tearing of the composition 212 during expansion as it allows for more material between adjacent struts.

The variation of the support member 202 illustrated in FIG. 3A includes control segments 210 which permit the support member 200 to assume a desired shape upon deployment. As will be described herein, the control segments 210 limit expansion of a portion of the implant (in this case the mid portion 208) as well as enable the implant to expand in a uniform manner. Although FIG. 3A illustrates the entire implant 200 as being covered by the composition 212, it is noted that the composition 212 may alternatively extend over portions of the support member 202.

FIG. 3B illustrates a side view of the implant 200 after expansion. In this variation, the control segments 210 restrain expansion at the mid portion 208. Because the proximal and distal portions 204, 206 are not restrained, upon expansion, the implant 200 forms a grommet shape as the control segments 210 unfold.

FIG. 3C illustrates a front view of an expanded implant 200. FIG. 3C shows the passageway having a hexagonal cross section. The cross-section, however, is not limited to such a shape. The cross section may be circular, oval, rectangular, elliptical, or any other multi-faceted or curved shape. Because of its shape, the implant 200 will have a variable diameter. The inner diameter ($D_1$) of the center section will be a minimum expanded diameter and the diameter of the implant at the expanded ends (D2) will be a maximum expanded diameter. The inner diameter (D1) when deployed, may range from 1 to 10 mm and perhaps, from 2 to 5 mm.

The variation of the implant 200 shown in FIGS. 3A-3C illustrate an additional feature of implants of the present invention. In some variations of the invention, implants 200 have a sufficiently small delivery state diameter so that they are delivered to the channel having a sufficiently small diameter profile but a relatively large axial length. Upon expansion, the implant's 200 minimum (internal) diameter is greater than or equal to its axial expanded length. This particular configuration provides several benefits. During deployment having a sufficient axial length permits proper centering of the implant 200 when inserted into the collateral channel, where improper centering could result in a inadequate placement about the airway walls. Upon expansion, as the implant 200 decreases in length it is able to grommet about the airway walls, thereby minimizing the amount of the structure that extends into the airway lumen. Simultaneously, maximizing the minimum internal expanded diameter (e.g., the diameter of the implant at the mid portion 208) allows for an implant that permits a sufficient amount of airflow.

FIGS. 4A-4C illustrate additional variations of implants 200 of the present invention. It is noted that in FIG. 4A, as in many additional figures below, the composition is not illustrated for sake of clarity. FIG. 4A shows a side view of a implant 200 in an un-deployed state. The variation shown in FIG. 4A is similar to that shown in FIG. 3 with the exception of that the proximal and distal portions 204, 206 are not tapered.

FIG. 4B illustrates a side view of the implant 200 of FIG. 4A when expanded. As shown, when viewed from the side, the opposing ends of the implant 200 may have a V, U, or similar shape. In some variations, the angles A1, A2 may vary and may range from, for example, 30 to 150 degrees, 45 to 135 degrees and perhaps from 30 to 90 degrees. Moreover, the angle A1 may be different than angle A2. Additionally, the angle corresponding to each proximal extension member may be different or identical to that of another proximal extension member. Likewise, the angle corresponding to each distal extension member may be different or identical to that of another distal extension member. FIG. 4B also illustrates the implant 200 having a length L that decreases upon expansion of the implant 200.

The length of the implants of the present invention will depend upon their intended site of implantation. Variations of implants may have lengths ranging from between 2-20 mm. Furthermore, although the figures illustrate the proximal and distal portions of the implant as being symmetric about its center, the implant is not limited to such a configuration.

Furthermore, the implant of the present invention may have any number of extension members on each end device. The number of extension members on each end may range from 2-10. Also, the number of proximal extension members may differ from the number of distal extension members for a particular implant. The extension members may be symmetrical or non-symmetrical about the center section. The proximal and distal extension members may also be arranged in an in-line pattern or an alternating pattern. The extension members or the center section may also contain barbs or other similar configurations to increase adhesion between the implant and the tissue. The extension members may also have openings to permit tissue in-growth for improved retention.

Control Members:

Variations of the implant 200, as seen in shown in FIGS. 3-6 also includes diametric-control segments, tethers, or leashes 210 to control and limit the expansion of the a portion of the implant 200 when expanded. The shape of the center-control segment 210 typically bends, when the implant radially expands, until it is substantially straight or unfolded. Such a center-control segment 210 may be circular or annular shaped in its folded or unexpanded shape. However, its shape may vary widely and it may have, for example, an arcuate, semi-circular, v-shape, u-shape, s-shape, sinusoidal shape, or other type of shape which limits the expansion of the implant upon unfolding.

The control members 210 assist the implant 200 in assuming a uniform non-cylindrical expanded shape. For example, as a balloon expands the implant 200 there will be variation in the amounts of expansion of various cells (i.e., where a cell is typically defined by an area surrounded by a number of joined struts—as an example refer to FIG. 4C, the shaded portion representing the cell 216) of the implant 200. If one cell expands at an increased amount relative to the remaining cells, once the control member 210 fully unfolds, the cell will be unable to further expand. Thus, the expansion force, as applied by the balloon, is re-directed to a remaining part of the implant 200. It should be noted that while the control members substantially straighten, there may be a residual bend or "kink" in the control member when expanded.

Typically, one end of the control segment 210 is attached or joined to one location (e.g., a first rib) and the other end of the center-control segment is connected to a second location (e.g., a rib adjacent or opposite to the first rib). However, in alternate variations, the center-control segments may have other constructs. For example, the center-control segments may connect adjacent or non-adjacent center section members. Further, each center-control segment may connect one or more ribs together. The center-control segments may further be doubled up or reinforced with ancillary control segments to provide added control over the expansion of the center section. The ancillary control segments may be different or identical to the primary control segments.

Referring back to FIG. 3B, which illustrates the implant 200 in its deployed configuration, the center-control segments 210 may bend, unfold, straighten, or otherwise deform until they maximize their length (i.e., unfold to become substantially straight) such as the center-control segments 210 shown in FIG. 3B. However, as discussed above, the invention is not so limited and other types of center-control segments may be employed.

Figure 5A:
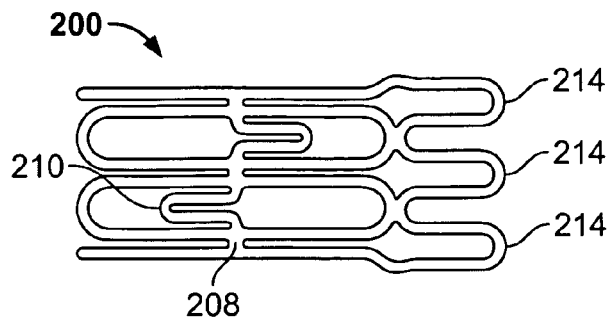
Figure 5B:
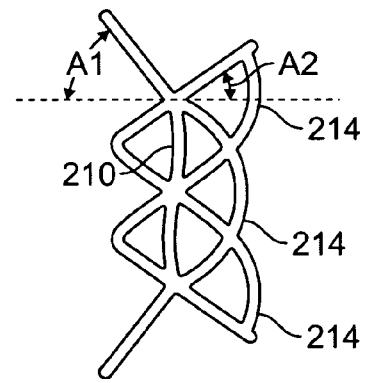
Figure 5C:
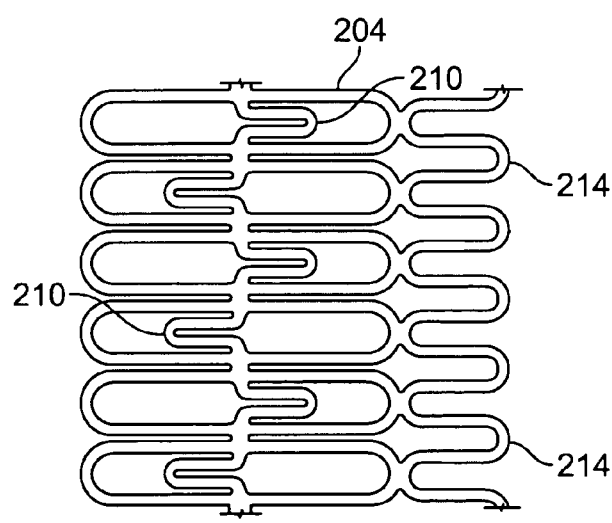

As shown in FIGS. 5-6, control segments 210 may also be used to join and limit the expansion of various portions of the implant 200. For example, in FIGS. 5A-5C, control segments may be placed elsewhere on the implant 200. For example, FIG. 5A illustrates control segments 210 located in an alternating pattern at the mid portion 208 of the implant 200. The implant 200 also includes additional control segments 214 located on an end of the implant 200. As shown in FIG. 5B, upon expansion of the implant 200 the end control segments 214 cause the respective end portion to form an angle A2 that is different from an angle A1 at the opposite unrestrained end.

Figure 6A:
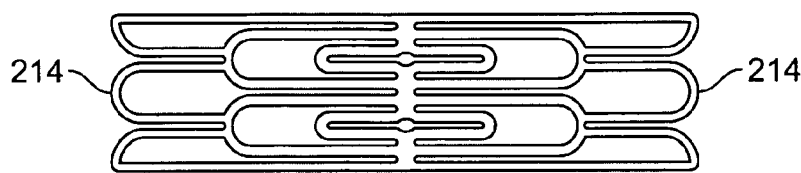
Figure 6B:
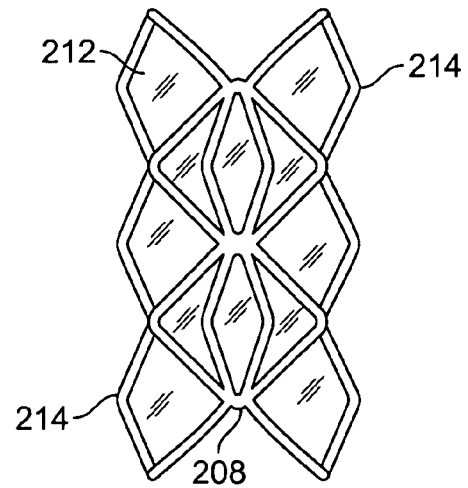

FIG. 6A illustrates an implant 200 similar to that of FIG. 3 with additional control segments 214 located at both ends of the implant 200. FIG. 6B illustrates the implant 200 of 6A in an expanded state. Although the control segments are illustrated to have equal lengths, any length may be selected. For example, adjacent control segments may have different lengths, or opposing control segments (e.g., those located on opposing ends) may have different lengths.

FIG. 7A illustrates another variation of the invention. Like previous variations of the implant 200 (e.g., FIGS. 3-6), the support member 202 may comprise a plurality of members forming a number of cells 216 where each cell 216 is joined to an adjacent cell at the mid portion 208 and the proximal and distal portions are unconnected. The cells 216 are located in a circumferential manner about an axis of the implant and further include at least one control member 210 having a serpentine configuration. Upon expansion of the cell, the control member 210 straightens or unfolds to limit expansion of the cell 216. For illustrative purposes, the composition is not illustrated in FIGS. 7A and 7B.

The variation of FIGS. 7A and 7B differ from previously described implants as the proximal 204 and distal 206 portions are of different sizes. The larger sized portion 206 may be useful in separating parenchymal tissue or providing a larger anchoring structure when implanted (as shown in FIG. 7B.)

FIG. 7C illustrates the implant 200 of FIGS. 7A and 7B having a composition 218 as described herein. As illustrated, variations of the invention include composition 218 that are only placed over a portion of the implant 200.

In any variation of the invention, the control segments, as with other components of the implant, may be added or mounted to the implant or alternatively, they may be integral with the implant. That is, the control segments may be part of the implant rather than separately joined to the implant with adhesives or welding, for example. The control segments may also be mounted exteriorly or interiorly to the members to be linked. Additionally, sections of the implant may be removed to allow areas of the implant to deform more readily. These weakened areas provide another approach to control the final shape of the deployed implant. Details for creating and utilizing weakened sections to control the final shape of the deployed implant may be found in U.S. Pat. Ser. No. 09/947,144 filed on Sep. 4, 2001 which is hereby incorporated by reference in its entirety.

The implant described herein may be manufactured by a variety of manufacturing processes including but not limited to laser cutting, chemical etching, punching, stamping, etc. For example, the implant may be formed from a tube that is slit to form extension members and a center section between the members. One variation of the implant may be constructed from a metal tube, such as stainless steel, 316L stainless steel, titanium, tantalum, titanium alloy, nitinol, MP35N (a nickel-cobalt-chromium-molybdenum alloy), etc. Also, the implant may be formed from a rigid or elastomeric material that is formable into the configurations described herein. Also, the implant may be formed from a cylinder with the passageway being formed through the implant. The implant may also be formed from a sheet of material in which a specific pattern is cut. The cut sheet may then be rolled and formed into a tube. The materials used for the implant can be those described above as well as a polymeric material, a biostable or implantable material, a material with rigid properties, a material with elastomeric properties, or a combination thereof. If the implant is a polymeric elastic tube (e.g. a thermoplastic elastomer), the implant may be extruded and cut to size, injection molded, or otherwise formed.

Additionally, the implants described herein may be comprised of a shape memory alloy, a super-elastic alloy (e.g., a NiTi alloy), a shape memory polymer, or a shape memory composite material. The implant may be constructed to have a natural self-assuming deployed configuration, but is restrained in a pre-deployed configuration. As such, removal of the restraints (e.g., a sheath) causes the implant to assume the deployed configuration. A implant of this type could be, but is not limited to being, comprised from an elastic polymeric material, or shape memory material such as a shape memory alloy. It is also contemplated that the implant could comprise a shape memory alloy such that, upon reaching a particular temperature (e.g., 98.5° F.), it assumes a deployed configuration.

Also, the implant described herein may be formed of a plastically deformable material such that the implant is expanded and plastically deforms into a deployed configuration. The implant may be expanded into its expanded state by a variety of devices such as, for example, a balloon catheter.

The implant's surface may be modified to affect tissue growth or adhesion. For example, an implant may comprise a smooth surface finish in the range of 0.1 micrometer to 0.01 micrometer. Such a finish may serve to prevent the implant from being ejected or occluded by tissue overgrowth. On the other hand, the surface may be roughened or porous. The implant may also comprise various coatings and polymeric layers as discussed below.

Composition

As discussed above, the implants of the present invention may include a composition or polymeric layer that includes a bio-active substance or combination of bioactive substances. One purpose of the composition is to assist in modifying the healing response as a result of the trauma to lung tissue resulting from creation of the collateral channel. The composition may also serve other purposes as well. For example, the composition may assist in controlling of bacteria, prevent irritation of the tissue near the implant, or may carry additional bio-active substances.

The term lung tissue is intended to include the tissue lining the airway, the tissue beneath the lining, and the tissue within the lung but exterior to the airway (e.g., lung parenchyma.) In modifying the healing response it is fundamentally desirable to further the patency of the channel to allow sufficient flow of trapped gasses through the implant into the airways. A discussion of the bio-active substances is found below.

FIGS. 3A and 3B illustrate an example an implant 200 having a composition 212. The composition may comprise a polymeric layer which acts as a carrier for various bioactive or other agents as described herein. Alternatively, or in combination, the polymeric layer may function as a tissue barrier to inhibit growth of tissue into the conduit/implant. In an additional variation, the support member may be fabricated from a polymeric material having the bio-active substance incorporated directly therein. The composition 212 prevents tissue in-growth from occluding the collateral channel or passage of the implant 200. The polymeric layer 212 may coaxially cover the center section from one end to the other or it may only cover one or more regions of the implant 200. The composition 212 may completely or partially cover the implant 200. The composition 212 may be located about an exterior of the implant's surface, about an interior of the implant's surface.

Alternatively, or in combination, as shown in FIGS. 8A and 8B, the composition 212 may be located within an opening or pocket 220 in the support structure 202 of the implant. In such a case, the pocket 220 will have a barrier (e.g., polymeric or other porous material) that either degrades to allow the composition or bioactive substance to be delivered from the implant, or acts as a diffusible barrier to deliver the composition or bioactive substance.

The composition should be selected to accommodate the significant expansion of the implant. Examples of such polymers include, but are not limited to, thermoplastic polymers, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof.

Examples of bioabsorbable polymers include but are not limited to poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly(amino acids), cyanoacrylates, poly(trimethylene carbonate), poly(iminocarbonate), copoly(ether-esters) (e.g., PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, fluorosilicones, and polyesters could be used. Also, hydrogels may be used to carry the drug.

Examples of other types of polymers that may be useful include but are not limited to polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins, polycarbonates; polyoxymethylenes; polyimides; polyethers; epoxy resins, polyurethanes; rayon; rayon triacetate; cellulose, cellulose acetate, cellulose butyrate; cellulose acetate butyrate; cellophane; cellulose nitrate; cellulose propionate; cellulose ethers; and carboxymethyl cellulose. It may be possible to dissolve and cure (or polymerize) these polymers on the implant so that they do not leach into the tissue and cause any adverse effects on the tissue.

The coatings may be applied, for example, by either painting, dip coating, molding, spin-coating, transfer molding or liquid injection molding. Alternatively, the polymeric layer may be a tube of a material and the tube is placed either over and/or within the implant. The polymeric layer may then be bonded, crimped, heated, melted, shrink fitted or fused to the implant. The polymeric layer may also be tied to the implant with a filament of, for example, a suture material.

Still other techniques for attaching the polymeric layer include: solvent swelling applications and extrusion processes; wrapping a sheet of material about the implant, or placing a tube of the material about the implant and securing the tube to the implant. The polymeric layer may be secured on the interior of the implant by positioning a sheet or tube of material on the inside of the center section and securing the material therein.

The composition may also be formed of a fine mesh with a porosity or treatment such that tissue may not penetrate the pores. For example, a ChronoFlex™ DACRON® or TEFLON® mesh having a pore size of 100-300 microns may be saturated with collagen or another biocompatible substance. This construct may form a suitable polymeric layer. The mesh may be coaxially attached to a frame such as the open frame structures disclosed above. Still other suitable frames include a continuous spiral metallic or polymeric element.

Bioactive Substances:

As discussed above, the bio-active substance or combination of bioactive substances is selected to assists in modifying the healing response as a result of the trauma to the lung tissue resulting from creation of the collateral channel. As noted above, the term lung tissue is intended to include the tissue lining the airway, the tissue beneath the lining, and the tissue within the lung but exterior to the airway (e.g., lung parenchyma.) The purpose of modifying the healing response is to further extend the patency of the channel or implant to increase the duration which trapped gasses may exit through the implant into the airways. The term antiproliferative agent is intended to include those bioactive substances that directly modify the healing response described herein.

The bioactive substances are intended to interact with the tissue of the surgically created channels and in particular, lung tissue. These substances may interact with the tissue in a number of ways. They may, for example, 1.) accelerate cell proliferation or wound healing to epithelialize or scar the walls of the surgically-created channel to maintain its patent shape or 2.) the substances may inhibit or halt tissue growth when a channel is surgically created through an airway wall such that occlusion of the channel due to tissue overgrowth is prevented. Additionally, other bioactive agents may inhibit wound healing such that the injury site (e.g., the channel or opening) does not heal leaving the injury site open and/or inhibit infection (e.g., reduce bacteria) such that excessive wound healing does not occur which may lead to excessive tissue growth at the channel thereby blocking the passageway.

A variety of bioactive substances may be used alone or in combination with the devices described herein. Examples of bioactive substances include, but are not limited to, antimetabolites, antithrobotics, anticoagulants, antiplatelet agents, thorombolytics, antiproliferatives, antinflammatories, agents that inhibit hyperplasia and in particular restenosis, smooth muscle cell inhibitors, growth factors, growth factor inhibitors, cell adhesion inhibitors, cell adhesion promoters and drugs that may enhance the formation of healthy neointimal tissue, including endothelial cell regeneration. The positive action may come from inhibiting particular cells (e.g., smooth muscle cells) or tissue formation (e.g., fibromuscular tissue) while encouraging different cell migration (e.g., endothelium, epithelium) and tissue formation (neointimal tissue).

Still other bioactive agents include but are not limited to analgesics, anticonvulsives, anti-infectives (e.g., antibiotics, antimicrobials), antineoplastics, H2 antagonists (Histamine 2 antagonists), steroids, non-steroidal anti-inflammatories, hormones, immunomodulators, mast cell stabilizers, nucleoside analogues, respiratory agents, antihypertensives, antihistamines, ACE inhibitors, cell growth factors, nerve growth factors, anti-angiogenic agents or angiogenesis inhibitors (e.g., endostatins or angiostatins), tissue irritants (e.g., a compound comprising talc), poisons (e.g., arsenic), cytotoxic agents (e.g., a compound that can cause cell death), various metals (silver, aluminum, zinc, platinum, arsenic, etc.), epithelial growth factors or a combination of any of the agents disclosed herein.

Examples of agents include pyrolitic carbon, titanium-nitride-oxide, taxanes, fibrinogen, collagen, thrombin, phosphorylcholine, heparin, rapamycin, radioactive 188Re and 32P, silver nitrate, dactinomycin, sirolimus, everolimus, Abt-578, tacrolimus, camptothecin, etoposide, vincristine, mitomycin, fluorouracil, or cell adhesion peptides. Taxanes include, for example, paclitaxel, 10-deacetyltaxol, 7-epi-10-deacetyltaxol, 7-xylosyl-10-deacetyltaxol, 7-epi-taxol, cephalomannine, baccatin III, baccatin V, 10-deacetylbaccatin III, 7-epi-10-deacetylbaccatin III,docetaxel.

Of course, bioactive materials having other functions can also be successfully delivered in accordance with the present invention. For example, an antiproliferative agent such as methotrexate will inhibit over-proliferation of smooth muscle cells and thus inhibit restenosis. The antiproliferative is desirably supplied for this purpose until the tissue has properly healed. Additionally, localized delivery of an antiproliferative agent is also useful for the treatment of a variety of malignant conditions characterized by highly vascular growth. In such cases, an implant such as a implant could be placed in the surgically created channel to provide a means of delivering a relatively high dose of the antiproliferative agent directly to the target area. A vasodilator such as a calcium channel blocker or a nitrate may also be delivered to the target site. The agent may further be a curative, a pre-operative debulker reducing the size of the growth, or a palliative which eases the symptoms of the disease. For example, tamoxifen citrate, Taxol® or derivatives thereof, Proscar®, Hytrin®, or Eulexin® may be applied to the target site as described herein.

Variations of the invention may also include fibrinolytics such as tPA, streptokinase, or urokinase, etc. Such fibrinolytics prevent or reduce the accumulation of fibrin within the opening. Accumulation of fibrin in the opening may result from inflammation of the tissue. The fibrin may form a structure which makes it easier for tissue to grow into the opening using the fibrin structure as a framework. Use of fibrinolytics, either topically, locally, or on the implant, serves to remove or hinder the network of fibrin from forming within the opening (or implant) and therefore aids in modifying the healing response.

In the event that poisonous and toxic compounds are delivered, they should be controlled so that inadvertent death of tissue does not occur. The poisonous agent should be delivered locally or only be effective locally. One method for delivering the bioactive agent locally is to associate the bioactive agent with an implant. For example, the implants described herein may include a bioactive substance or medicine deposited onto the interior, the exterior, or both the interior and exterior surfaces of the implant. The bioactive substance may remain on the implant so that it does not leach. Cells that grow into the surgically created channel contact the poison and die. Alternatively, the bioactive agent may be configured to gradually elute as discussed below.

When used in the lungs, the implant modifies the healing response of the lung tissue (e.g., at the site of newly created hole/channel) for a sufficient time until the healing response of the lung tissue subsides or reduces such that the hole/channel becomes a persistent air path. For example, the implant and bioactive substance will modify the healing response for a sufficient time until the healing response is reduced and, from a visual observation, the body treats the opening essentially as a natural airway passage rather than as an injury to the airway wall.

To illustrate the above, FIGS. 11A-11B show histology from animal models. The histology is a cross sectional slice of the airway wall 110 and lung parenchyma 116. In each slide, the collateral channel 112 was created in the airway wall 110 and extended into the lung parenchyma 116. The implant (which was removed for histology and is not shown) was placed in the channel 112 so as to create an airflow path (as demonstrated by the arrows 114) from the lung parenchyma 116 through the airway wall 110.

FIG. 11A illustrates a histology sample from a site two weeks subsequent to the creation of a channel and implantation with a device. In this site, the device included a polymeric coating but no bio-active substance. This site was also given a single local treatment of a bioactive substance (mitomycin) subsequent to creation of the channel 112. As shown, two weeks subsequent to the procedure, the healing process of the lung tissue already caused a considerable amount of fibrosis 120 between the channel 112 and lung parenchyma 116. From the figure, the fibrosis appears as a darker tissue that is adjacent to the lung parenchyma 116. The presence of this fibrosis 120 strongly suggests that air would not be able to flow from the lung parenchyma 116 through the channel 112.

FIG. 11B illustrates a histology sample from a site 18 weeks subsequent to the creation of a channel and implantation with an implant of the present invention (an example of which is discussed below.) As evident from the figure, the channel 112 remained significantly unobstructed with only a minimal discontinuous layer of fibrosis 120.

In one variation of the invention which modifies the healing response as describe above, the implant provides a steady release rate of bio-active substance as well as has a sufficient amount of available bio-active substance to modify the healing response of the lung tissue. As noted herein, the term lung tissue is intended to include the tissue lining the airway, the tissue beneath the lining, and the tissue within the lung but exterior to the airway (e.g., lung parenchyma.) Such a delivery profile allows for a concentration gradient of drug to build in these tissues adjacent to the delivery site of the implant.

It is believed that forming the concentration gradient affects the healing response of the lung tissue so that the implant does not become occluded as a result of the healing response. Because the implant is often placed in the airway wall it is exposed to the healing process of the multiple tissues. Providing a sufficient amount of bio-active substance allows for the formation of a concentration of the bio-active substance across these various tissues. In one variation of the invention it is believed that the fluids from these tissues enter into the composition layer of the device. The fluids then combine with the bio-active substances and migrate out of the composition layer to settle into the lung tissue. A concentration gradient forms when the drug 'saturates' local tissue and migrates beyond the saturated tissues. Furthermore, by providing a sufficient delivery rate, the healing response may be affected or suppressed during the critical time immediately after the wounding caused by creation of the collateral channel when the healing response is greatest.

To select a proper combination of drug and polymer, it is believed that the solubility parameter of the polymer must be matched with the bio-active substance to provide an acceptable slow elution rate from the polymer. Next, the polymer itself must be selected to have the proper attributes, such as a proper diffusion coefficient (to slow fluid entering and departing from the implant), and proper mechanical expansion properties (to allow for the significant expansion of the polymer to accommodate formation of the grommet shape.)

The solubility parameter is defined as the square root of the cohesive energy of the molecules in a compound. The level of control that a polymer has over the elution of a drug is the difference between the solubility parameters of the polymer and the solubility parameter of the drug. To select a polymer with the approximate diffusion a polymer with a high internal density could be selected to be less permeable to a complex molecule such as paclitaxel. Using a polymer with high internal density also accommodated the significant expansion required of the polymer to form the structure necessary to grommet about the airway wall. An example of the polymer selection is found below.

It is also important to note that paclitaxel is a taxane that is regarded as a microtubule stabilizer. The benefits of a microtubule stabilizing substance for use in vascular drug eluting stents is discussed, for examples, in U.S. Pat. No. 5,616,608 to Kinsella et al. This type of drug operates to enhance microtubule polymerization which inhibits cell replication by stabilizing microtubules in spindles which block cell division. In contrast to the vascular applications, the implant for use in the present invention may use microtubule destabilizing substances such as taxenes (e.g., paclitaxel) as well as those microtubule destabilizing substances that are believed to promote microtubule disassembly in preventing cell replication. Such destabilizing substances include, but are not limited to vincristine, vinblastine, podophylotoxin, estramustin, noscapine, griseofulvin, dicolmarol, a vinca alkaloid, and a combination thereof.

Additionally, the exterior surface of the implant may be treated via etching processes or with electrical charge to encourage binding of the bioactive substance of the implant. The exterior surface may also be roughened to enhance binding of the medicine to the surface as discussed in U.S. Patent Application Publication No. 2002/0098278. See also U.S. Patent Application Publication Nos. 2002/0071902, 2002/0127327 and U.S. Pat. No. 5,824,048 which discuss various techniques for coating medical implants.

Although the implant may comprise a frame or body with a bioactive matrix disposed or otherwise associated therewith, the invention is not so limited. In one variation, the support member is formed from a polymer and the composition is joined to the polymeric support member. Alternative, the bioactive substances may be placed directly onto the polymeric support member.

Various additional substances may be used incorporated into the device to reduce an adverse reaction resulting from possible contact with the implant and the airway wall. Adverse reactions include, but are not limited to, granulation, swelling, and mucus overproduction. These substance may also be inhaled, injected, orally applied, topically applied, or carried by the implant. These substances may include anti-imflammatory, infection-fighting substances, steroids, mucalytics enzymes, and wound healing-accelarating substances. Examples of these substances include but are not limited to, acetylcysteine, albuterol sulfate, ipratropium bromide, dornase alfa, and corticosteroids.

As noted above, conventional vascular drug eluting devices are not designed for exposure multiple tissue environments. Moreover, those devices are placed in an environment where a constant flow of blood creates an environment requiring a different delivery mechanism and rate. As noted, herein, experiments with conventional coronary drug eluting implants demonstrated that such devices were unsuitable FIG. 12 illustrates data from a pre-clinical animal model evaluating the wound healing response, under pre-clinical protocol (QT-305), using an implant w/o any antiprliferative substance, a paclitaxel coronary Stent (manufactured by Boston Scientific under the name Taxus®), and a sirolimus coronary stent (manufactured by Johnson & Johnson under the name of Cypher®) In comparison, experiments using implants according to the present invention, QT-345 and QT-362 were conducted. The implant w/o intiproliferative substance, the paclitaxel coronary stent, and the sirolimus coronary stent reduced to at least 50% patency without stabilization (i.e., the determination was made that 100% closure would occur.) The chart indicates closure of these devices given a criteria that at least half of the implanted devices closed with tissue and the trend indicated that full closure of the devices would occur. In contrast, the implants according to the present invention maintained 88% patency of the openings @ 12 weeks (QT-362) and 69% patency @ 18 weeks (QT-345). In both of these latter cases, repeated inspection determined that the healing response (as evidenced by the closure rate) of the implants stabilized. Furthermore, for QT-362, 2 specimens maintained 100% patency while 1 specimen maintained 75% patency. For QT-345, no decline in patency occurred for the last 6 weeks of the trial.

It is important to note that, to obtain data and a histology, applicants terminated QT-304 at 7 weeks (42 days), QT-362 at 12 weeks, and QT-345 at 18 weeks. Yet, based on the trend and closure of the devices, full closure would have occurred soon after 7 weeks for all devices in QT-304. In contrast, based on the stabilization of both the trend and relative patency of the devices in QT-362 and QT-345, patency of the devices in these trials would have extended well beyond the respective 12 and 18 weeks. In the above protocols, patency of the implants were determined visually using a bronchoscope advanced to the implant site.

Visualization Feature

As discussed above, when placed into an airway wall, the implant of the present invention is usually placed using a bronchoscope under direct visualization. In such a procedure, the direct visualization only permits viewing of the interior of the airway and the care must be taken to place the implant such that during expansion, the implant properly deploys about the airway wall. Also, care must be taken not to advance the implant/balloon catheter too far into the opening into the airway wall. Improper advancing of the implant/balloon could potentially result in a pneumothorax or pneumomediastinum.

To address the above problem, as illustrated in previous figures, the implant 200 may also include a visualization mark 218. The visualization marker 218 is visually apparent during a procedure and gives the medical practitioner an indication when the implant/balloon is advanced to the proper location. In this manner, the visualization mark 218 facilitates alignment and deployment of the implants into collateral channels.

The visualization mark 218 may be a ring of biocompatible polymer and may be selected to provide contrast so that it may be identified as the medical practitioner views the device through a endoscope or bronchoscope. For example, the bronchoscope will usually contain a light-source that illuminates the target area. Therefore, the visualization mark may be something that reflects or refracts the light in a different manner from the remainder of the implant. In one variation, the visualization mark may be the same color as the remainder of the device, or partially transparent, or entirely transparent, but is identifiable because the mark reflects or refracts light differently than the remainder of the device. Also, the visualization feature may protrude from the center section or it may be an indentation(s). The visualization mark may also be a ring, groove or other physical feature on the implant. Moreover, the visualization feature may be continuous or comprise discrete segments (e.g., dots of segments).

The visualization feature may be made using a number of techniques. In one example, the mark is a ring formed of silicon and is white. The polymeric ring may be spun onto the polymeric layer. For example, a clear silicon barrier may be coated onto the implant such that it coaxially covers the implant. Next, a thin ring of white material such as a metal oxide suspended in clear silicon may be spun onto the silicon coating. Finally, another coating of clear silicon may be applied to coat the white layer. The implant thus may include upwards of 1-3 layers including a polymeric layer, a visualization mark layer, and a clear outer covering. In another example the mark is a ring formed by of silicon and is black. In another example the mark is a ring formed by suspending gold particulates in the polymer as shown in FIG. 9A.

The shape of the visualization mark is not limited to a thin ring. The visualization mark may be large, and cover an entire half of the implant as shown in FIG. 9B. The visualization mark may, for example, be a white coating disposed on the proximal or distal half of the implant, The visualization mark thus may extend from an end of the extension members to the center section of the implant. As explained in more detail below, when such a device is deposited into a channel created in lung tissue, the physician may observe when one-half of the implant extends into the channel. This allows the physician to properly actuate or deploy the implant in the tissue wall.

In most variations of the invention, the visualization mark is made to stand out when viewed with, for example, an endoscope. The implants may also have additional imaging enhancing additives to increase non-direct imaging, such as flouroscope or radioscope viewing. It is also contemplated that other elements of the implant can include visualization features such as but not limited to the extension members, polymeric layer, control segments, etc.

In some variations of the invention, it was found that incorporation of a bioactive or other substance into the coating caused a coloration effect in the composition layer (e.g., the polymer turns white ). This coloration obscures the support member structure in the layer making it difficult to identify the edges and center of the support member or implant. As discussed herein, placement of the implant may depend upon positioning the center of the implant within the opening in tissue. If the support member structure is identifiable, then one is able to visually identify the center of the implant. When the composition colors obscures the support member or renders the implant otherwise opaque, it may become difficult to properly place the device. This may be especially true when the composition layer extends continuously over the support member.

Additionally, the coloration may render the visualization mark difficult to identify especially under direct visualization (e.g., using a endoscope) In some cases it was undesirable to simply add additional substances on or in the composition layer for marking because such substances could possibly interfere with the implant's ability to deliver the substance as desired. To address these issues, a variation of the invention includes e delivery device for delivering an expandable implant (such as those described herein and in the cases referenced herein), where the delivery device includes an expandable member having an expandable implant located about the expandable member. Where the implant and the expandable member are of different visually identifiable colors or shades such that the distinction is easy to identify under endoscopic or bronchoscopic viewing.

In one example, as shown in FIG. 9C, a balloon catheter has a colored sleeve 306 located about the ballon. The sleeve 306 comprises a visually identifiable color where selection of the colors should ease identification of the implant in an endoscopic visualization system (e.g., blue or a similar color that is not naturally occurring within the body.) The implant is placed about the sleeve 306 where the proximal and distal areas of the implant would be identifiable by the difference in color. Such a system allows a medical practitioner to place the implant 200 properly by using the boundary of the implant 200 to guide placement in the tissue wall. The sleeve 306 may be fashioned from any expandable material, such as a polymer. Optionally, the sleeve 306 may also provide an elastic force to return the balloon to a reduced profile after expansion of the balloon. Such a system allows for identification without affecting the properties of the implant.

It should be noted that variations of the invention include coloring the balloon itself, or other expandable member, a color that meets the above criteria.

In another variation, the visualization mark may comprise providing a contrast between the implant and a delivery catheter. In one example the implant appears mostly white and while mounted on a contrasting color inflation balloon. In this example the implant would be placed over a blue deflated balloon catheter. The proximal and distal areas of the implant would be flanked by the deflated blue balloon, thus giving the appearance of a distinct distal and proximal end of the implant. This would allow a physician to place the implant properly by using the blue flanks as a guide for placing the center white portion in the tissue wall. Similarly, a colored flexible sheath covering the balloon would also suffice.

It is noted that while the visualization features described above are suitable for use with the implants described herein, the inventive features are not limited as such. The features may be incorporated into any system where placement of an implant under direct visualization requires clear identification of the implant regardless of the whether the implant is opaque or colored.

Valves and Barriers within Implants

The implants may further comprise various structures deposited within the passageway. For example, as shown in FIG. 9, an implant may include a valve 224. The valve 224 may be positioned such that it permits expiration of gas from lung tissue but prevents gas from entering the tissue. The valve 224 may be placed anywhere within the passageway of the implant. The valve 224 may also be used as bacterial in-flow protection for the lungs. The valve 224 may also be used in combination with a bioactive or biostable polymeric layer/matrix and the polymeric layer may be disposed coaxially about the implant. Various types of one way valves may be used as is known to those of skill in art.

One example of the one-way valve 224 is such that when air is a valve as shown in FIG. 10A. The geometry of the valve is such that when air is passed through the valve 224 the bill members deflect. When air places pressure on the closed side the geometry of the bills place a force onto the opening preventing air from flowing through.

Additionally, a valve could be used to prevent fluid such as mucus from flowing into the passage and into the parenchyma. Such a valve could be configured and could operate similarly to the one described above for gas flow.

FIG. 10B illustrates another variation of the invention 200 having a barrier which may serve as an anti-bacterial barrier, or to preserve sterility of the parenchymal tissue adjacent to the implant.

The above illustrations are examples of the invention described herein. Because of the scope of the invention, it is specifically contemplated that combinations of aspects of specific embodiments or combinations of the specific embodiments themselves are within the scope of this disclosure.

EXAMPLE

Implant

Implants comprising stainless steel mesh frame fully encapsulated with a composition comprising silicon (as described below) and paclitaxel were implanted in several canine models. Visual observation indicated that, on average, the passage through the implants of the present invention remained unobstructed and were associated with significantly reduced fibrotic and inflammatory responses, in canine models, at a considerably higher rate than an implant without any drug adjunct or coronary drug eluting stents (as shown in FIG. 12).

The composition comprised approximately a 9% paclitaxel to silicone ratio with approximately 400 micrograms of paclitaxel per implant. Measurements found that approximately 30% of the paclitaxel released after 60 days. In general, for implants with the paclitaxel/silicon composition, observations of chronic inflammation, epithelial metaplasia and fibrosis were very mild.

For paclitaxel as the bioactive substances, polymers with solubility parameter between 5-25 (Mpa)^½ were believed to provide sufficient elution rates. The polymer used in the example device has good diffusivity for lipophilic drug (such as paclitaxel) because the side methyl group on the silicone may be substituted with more lipophilic hydrocarbon molecules containing vinyl group or groups for polymerization by platinum catalyst.

The composition for the example may be as follow: polymer part: polydimethylsiloxane, vinyldimethyl terminated, any viscosity; and/or polydimethylsiloxane, vinyldimethyl terminated, any viscosity. The cross-linker part: polydimethylsiloxane, any viscosity; and/or polydimethylsiloxane, any viscosity. Platinum catalyst part and/or cross-linker part: platinum; and/or platinum-divinyltetramethyldisiloxane complex in xylene, 2-3% Pt; and/or platinum-divinyltetramethylsiloxane complex in vinyl terminated polydimethylsiloxane, 2-3% Pt; and/or platinum-divinyltetramethyldisiloxane complex in vinyl terminated polydimethylsiloxane, ~1% Pt; platinum-Cyclovinylmethylsiloxane complex, 2-3% Pt in cyclic methyl siloxane.

These components may be combined in different ratios to make the polymer. The hydrocarbon side chain off the silicon back bone makes this polymer system unique and may result in a "zero-order"—like release profile. The amount of vinyl siloxane cross-linker may determine the rate of the drug release and diffusivity of the polymer to the drug. There are other types of poly dimethylsiloxanes such as: trimethylsiloxy terminated polydimethylsiloxane copolymer in various viscosities, (48-96%) dimethyl (4-52%) diphenylsiloxane copolymer in various viscosities, dimethylsiloxane-ethylene oxide copolymer, dimethyl diphenylsiloxane copolymer polymethylhydrosiloxane, trimethylsilyl terminated at various viscosities, (30-55%) methyldro- (45-70%) dimethylsiloxane copolymer at various viscosities, polymethylphenlsiloxane, polydimethylsiloxane silanol terminated at various viscosities, polydimethylsiloxane aminopropyldimethyl terminated at various viscosities. For paclitaxel a release profile was found to be acceptable with a polymer system consisting of polydimethylsiloxane vinyl terminated at various viscosity and a range of platinum-mono, di, tri and/or tetrametramethyldisiloxane complex.

We claim:

1. An implant configured for maintaining an artificial opening in a wall of an airway, the implant comprising:

a support member having a proximal portion, a mid portion, a distal portion, and an interior passage extending therethrough, where the proximal, and distal portions are all expandable and the proximal and distal portions are expandable to a greater size than the mid portion, where the mid portion includes a plurality of members forming a mesh having a plurality of interstices and wherein the proximal and distal portions are expandable such that the support member forms a grommet shape and secures the support member about a perimeter of the artificial opening in the airway wall; and a means for maintaining patency of the artificial opening in the airway wall at 12 weeks following deployment of the implant in the artificial opening in the airway wall.

2. The implant of claim 1. where said means for maintaining patency of the artificial opening in the airway wall includes a composition. and where said composition comprises an antiproliferative agent and a polymer.

3. The implant of claim 2, where the composition comprises an amount of antiproliferative agent that does not exhibit substantial cytotoxicity but controls the healing response by suppressing hyperplasia of lung tissue, to maintain patency of an artificial opening located in the airway which allows for maintaining air passage between the opening and parenchyma for a sufficient time until the healing response of the lung tissue subsides such that the opening essentially becomes a natural airway passage.

4. The implant of claim 2, where the composition comprises both a release rate and an amount of antiproliferative substance sufficient to modify a healing response of the airway wall resulting from creation of the opening.

5. The implant of claim 2, where the polymer is selected from a group consisting of thermoplastic polymers, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA. polyortho-ester, polycapralactone, polyester, hydrogels, polystyrene, co-polymers of styrene-isobutylene-styrene, and combinations or blends thereof.

6. The conduit of claim 2, further comprising a dye located in the polymer to aid in identification of the implant during placement.

7. The implant of claim 2, where the composition fully covers an outer surface of the support member.

8. The implant of claim 7, where the polymer fully encapsulates an interior surface of the support member.

9. The implant of claim 2, where the support member comprises a second polymeric material.

10. The implant of claim 9, where the polymer and second polymeric material are bioabsorbable.

11. The implant of claim 1, where the support structure has at least one pocket where the antiproliferative substance is located in the pocket, and further comprising a polymer at least covering the pocket to act as a baffler to release.

12. The implant of claim 1. where the support member comprises a metallic material.

13. The implant of claim 1, further comprising folded control members disposed within said interstices of the mid portion, and where the folded control members form a shape selected from a group consisting of an s-shape, a u-shape, and a sinusoidal shape.

14. The implant of claim 2, where the antiproliferative agent comprises a microtubule stabilizing agent.

15. The implant of claim 14, where the microtubule stabilizing agent is paclitaxel.

16. The implant of claim 2, where the antiproliferative agent comprises a microtubule destabilizing agent.

17. The implant of claim 16, where the microtubule destabilizing agent is selected from the group comprising vincristine, vinblastine, podophylotoxin, estramustine, noscapine, griseofulvin, dicoumarol, a vinca alkaloid, and a combination thereof.

18. The implant of claim 2, where the antiproliferative agent comprises a substance selected from the group consisting of steroids, non-steroidal anti-inflammatories, and d-actinomycin, and a combination thereof.

19. The implant of claim 2, where the antiproliferative agent comprises a cytostatic agent.

20. The implant of claim 19, where the cytostatic agent is selected from the group consisting of: sirolimus, everolimus, ABT-578, biolimus, tacrolimus, and a combination thereof.

21. The implant of claim 1, further comprising a mucus affecting substance.

22. The implant of claim 21, where the mucus affecting substance is selected from a group consisting of mucolytics, rhDnase. and a combination thereof.

23. The implant of claim 1, further comprising at least one visualization mark disposed on a portion of the support member.

24. The implant of claim 23, where the visualization mark comprises a stripe circumferentially disposed about at least a portion the support member.

25. The implant of claim 1, further comprising a one-way valve in fluid communication with the interior passage.

26. The implant of claim 1, further comprising an antibiotic substance carried on or within the support member.

27. The implant of claim 1, further comprising a barrier located within the support member.

28. The implant of claim 1, further comprising a fibrin reducing substance.

29. The implant of claim 28, where the fibrin reducing substance is selected from a group consisting of streptokinase, urokinase, and tissue plasminogen activator.

30. An implant configured for maintaining an artificial opening in a wall of an airway, the implant comprising:
 a support member having a proximal portion, a mid portion, a distal portion, and an interior passage extending therethrough, where the proximal, and distal portions are all expandable and the proximal and distal portions are expandable to a greater size than the mid portion, such that the support member forms a grommet shape and secures the support member about a perimeter of the artificial opening in the airway wall; and
 a composition located on the support member, where the composition comprises approximately 400 micrograms of paclitaxel.

31. The implant of claim 30, where said composition comprises a polymer, and said composition has a ratio of paclitaxel to polymer of about 9%.

32. The implant of claim 30, where the implant comprises a size and amount of composition to maintain patency of the artificial opening in the airway wall at about 18 weeks following deployment of the implant in the artificial opening in the airway wall.

* * * * *